United States Patent [19]

Genain et al.

[11] Patent Number: 5,072,006

[45] Date of Patent: Dec. 10, 1991

[54] NOVEL BENZOPYRANYLPYRROLINONE DERIVATIVES

[75] Inventors: Gilles Genain, Issy-les-Moulineaux; Henri Pinhas, Paris, both of France

[73] Assignee: Recherche Syntex France S.A., France

[21] Appl. No.: 630,092

[22] Filed: Dec. 19, 1990

Related U.S. Application Data

[62] Division of Ser. No. 282,407, Dec. 9, 1989, Pat. No. 4,997,846.

[51] Int. Cl.$^5$ .............................................. C07D 311/68
[52] U.S. Cl. ........................................ 549/399; 549/404
[58] Field of Search ................................. 549/399, 404

[56] References Cited

U.S. PATENT DOCUMENTS

| | | | |
|---|---|---|---|
| 4,110,347 | 8/1978 | Watts | 260/345.2 |
| 4,238,501 | 12/1980 | Kabbe et al. | 549/404 |
| 4,363,811 | 12/1982 | Evans et al. | 549/399 |
| 4,391,815 | 7/1983 | Evans | 549/399 |
| 4,445,113 | 5/1984 | Evans et al. | 546/196 |
| 4,620,019 | 10/1986 | Cue, Jr. et al. | 549/404 |
| 4,629,734 | 12/1986 | Ashwood | 514/456 |
| 4,631,282 | 12/1986 | Cassidy | 514/254 |
| 4,640,928 | 2/1987 | Willcocks | 546/196 |

FOREIGN PATENT DOCUMENTS

| | | |
|---|---|---|
| 009912 | of 0000 | European Pat. Off. . |
| 273262 | of 0000 | European Pat. Off. . |
| 274821 | of 0000 | European Pat. Off. . |
| WO85/01290 | of 0000 | PCT Int'l Appl. . |

OTHER PUBLICATIONS

J. Med. Chem, vol. 582-1589 (1983).
J. Med. Chem, vol. 27, 1127-1131 (1984).
J. Med. Chem. vol. 29, 2194-2201 (1986).

*Primary Examiner*—C. Warren Ivy
*Assistant Examiner*—Ba K. Trinh
*Attorney, Agent, or Firm*—Brian Lewis; Tom M. Moran; David A. Lowin

[57] ABSTRACT

Compounds of the formula

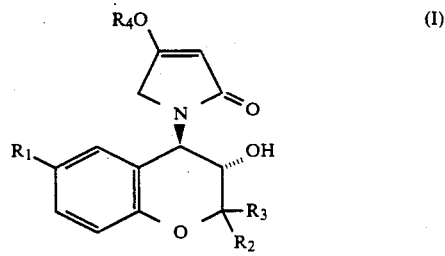

wherein:
  $R_1$ is cyano or nitro;
  $R_2$ and $R_3$ are independently hydrogen or lower alkyl; and
  $R_4$ is alkyl; alkenyl; optionally substituted phenyl or phenyl lower alkyl; —$(CH_2)_mOR_2$ or —$(CH_2)_mN(R_2)_2$; wherein m is an integer of 1-5 and $R_2$ is as defined above;
or a pharmaceutically acceptable ester thereof; are smooth muscle relaxants, particularly useful in the treatment of hypertension.

8 Claims, No Drawings

NOVEL BENZOPYRANYLPYRROLINONE DERIVATIVES

This is a division of pending application Ser. No. 07/282,407, filed Dec. 9, 1989, now U.S. Pat. No. 4,997,846, incorporated herein by reference.

BACKGROUND OF THE INVENTION

1. Field of the Invention

This invention relates to novel benzopyranylpyrrolinone derivatives that are smooth muscle relaxants, and are thus useful as agents in the treatment of essential and pulmonary hypertension, congestive heart failure, angina, smooth muscle spasm, in particular cerebro-vasospasm, cardiac arrhythmia, stroke, dysmenorrhea, renal failure, peripheral vascular occlusive disease, unstable bladder and urinary retention, nocturnal asthma, and gastrointestinal disorders, in particular irritable bowel syndrome. Other indications include treatment of baldness.

2. Related Disclosures

Benzopyran derivatives are disclosed in the patent literature as having blood pressure lowering activity. For example see U.S. Pat. Nos. 4,048,317 and 4,647,670, European Patent Applications 076,075 and 172,352, and G.B. 1,548,222. A typical example is found in U.S. Pat. No. 4,446,113, which discloses a broad range of compounds having antihypertensive activity which are of the formula:

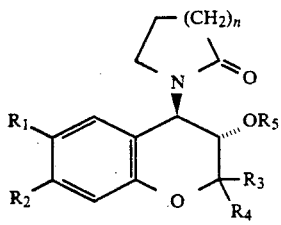

wherein:

One of $R_1$ and $R_2$ is hydrogen and the other is selected from the class of alkylcarbonyl, alkoxycarbonyl, alkylcarbonyloxy, alkylhydroxymethyl, nitro, cyano, chloro, trifluoromethyl, alkylsulphinyl, alkylsulphonyl, alkoxysulphinyl, alkoxysulphonyl, alkoxycarbonylamino, alkylcarbonylamino, or aminosulphinyl, aminosulphonyl or aminocarbonyl, the amino moiety being optionally substituted by one or two alkyl groups, or alkylsulphinylamino, alkylsulphonylamino, alkoxysulphinylamino or alkoxysulphonylamino or ethylenyl terminally substituted by alkylcarbonyl, nitro or cyano, or —C(alkyl)NOH or C(alkyl)NNH$_2$, the alkyl groups or alkyl moieties of alkyl-containing groups having from 1 to 6 carbon atoms;

one of $R_3$ and $R_4$ is hydrogen or alkyl having from 1 to 4 carbon atoms and the other is alkyl having from 1 to 4 carbon atoms, or $R_3$ and $R_4$ together with the carbon atom to which they are attached are spiroalkyl having from 3 to 6 carbon atoms;

$R_5$ is hydrogen, alkyl having from 1 to 3 carbon atoms or acyl having from 1 to 8 carbon atoms, and n is 1 or 2, the lactam group being trans to the OR$_5$ group.

Similar compounds bearing a hydroxy group on the pyrrolidin-2-one ring are disclosed in EP 274,821.

In the search for new drugs to treat a specific disease state a desirable goal is to find a class of compounds that effectively treat that disease state at lower dose levels than allowed by existing therapy, and/or are effective over a longer period of time. Compounds that are effective at low dose levels generally have a better therapeutic ratio, i.e. separate the desired activity from any undesired side effects, and compounds that are effective over a longer period of time eliminate the need for frequent (and inconvenient) administration of the drug.

It has now surprisingly been found that a structurally distinct class of benzopyran compounds has superior smooth muscle relaxant properties, in particular antihypertensive activity. This class of benzopyran compounds is characterized by the presence of a 3-pyrrolin-2-one ring substituted at the 4-position by an ether group. These compounds have been found to be more active and/or longer acting than those compounds previously known in the benzopyranpyrrolidin-2-one series.

SUMMARY OF THE INVENTION

One aspect of the invention concerns novel compounds represented by the formula

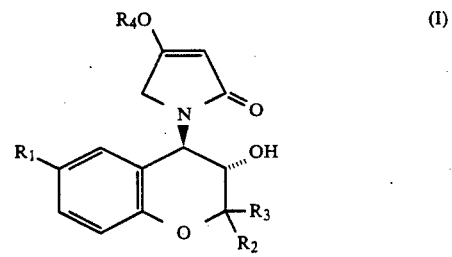

wherein:

$R_1$ is cyano or nitro;

$R_2$ and $R_3$ are independently hydrogen or lower alkyl; and $R_4$ is alkyl; alkenyl; phenyl or phenyl-lower-alkyl in which any phenyl group may be optionally substituted with one or two substituents chosen from lower alkyl, lower alkoxy, halo, trifluoromethyl and hydroxy; —(CH$_2$)$_m$OR$_2$ or —(CH$_2$)$_m$N(R$_2$)$_2$; wherein m is an integer of 1–5 and $R_2$ is as defined above;

or a pharmaceutically acceptable ester thereof.

Other aspects of the invention relate to pharmaceutical compositions containing a compound of formula (I), and to methods pertaining to the use of compounds of formula (I) and the use of compositions containing such a compound. A further aspect of the invention relates to optical isomers of the compounds of formula (I). Yet another aspect relates to the novel processes by which optical isomers or racemic mixtures of compounds of formula (I) are obtained.

DETAILED DESCRIPTION OF THE INVENTION

Definitions

"Alkyl" means a branched or unbranched saturated hydrocarbon chain containing 1 to 12 carbon atoms, such as methyl, ethyl, propyl, isopropyl, tert-butyl, n-hexyl, 2-methylheptyl, n-decyl, n-dodecyl and the like, unless otherwise indicated;

"Lower alkyl" means a branched or unbranched saturated hydrocarbon chain containing 1 to 4 carbon atoms, such as methyl, ethyl, propyl, isopropyl, tert-butyl, n-butyl and the like, unless otherwise indicated.

"Alkenyl" means a branched or unbranched hydrocarbon chain containing a double bond and having 2 to 12 carbon atoms, such as vinyl, allyl, but-3-en-1-yl, pent-2-en-1-yl, 4-methylpent-2-en-1-yl, dodec-5-en-1-yl and the like.

"Lower alkoxy" means the group —O—(lower alkyl), wherein lower alkyl is as herein defined.

"Halo" as used herein denotes fluoro, chloro, bromo, or iodo, unless otherwise indicated.

"Phenyl" as used herein encompasses all possible isomeric phenyl radicals optionally monosubstituted or disubstituted with a substituent selected from the group consisting of lower alkyl, lower alkoxy, hydroxy, trifluoromethyl and halo.

"Phenyl-lower-alkyl" as used herein denotes phenyl as defined herein attached to a lower alkyl group as defined herein, for example benzyl, 1-phenylethyl, 2-phenylethyl, 3-phenylpropyl, and the like.

"Optional" or "optionally" means that the subsequently described event or circumstance may or may not occur, and that the description includes instances where said event or circumstance occurs and instances in which it does not. For example, "optionally substituted phenyl" means that the phenyl may or may not be substituted and that the description includes both unsubstituted phenyl and substituted phenyl.

"Inert solvent" means a solvent in which a reaction may be carried out which will not itself react with the reactants. One of ordinary skill will recognize which solvents are inert for a particular reaction, and may be for example benzene, toluene, xylene, acetonitrile, dimethylformamide, dimethylsulfoxide, alcohols, esters, and the like.

"Pharmaceutically acceptable ester" as used herein refers to those non-toxic esters of a compound of formula (I) that are formed by reaction with an appropriate carboxylic acid or carboxylic acid derivative. Typical esters are those derived from formic acid, acetic acid, propionic acid, butyric acid, isobutyric acid, pivalic acid, hexanoic acid, optionally substituted benzoic acid, optionally substituted phenylacetic acid, and the like. The esters are prepared by methods well known in the art, for example by reacting the compound of formula (I) with the appropriate acid in the presence of an acid catalyst, for example sulfuric acid, hydrochloric acid, p-toluenesulfonic acid, and the like, or alternatively in the presence of a dehydrating agent, for example 1,3-dicyclohexylcarbodiimide. Alternatively the esters may be prepared by reacting the compound of formula (I) with the appropriate acid chloride or anhydride in the presence of a base at a suitable temperature, typically ranging from about −50° to 50° C., preferably about 0° C. to room temperature.

The compounds of this invention possess asymmetric centers and thus can be produced as mixtures of stereoisomers or as individual stereoisomers. The individual stereoisomers may be obtained by resolving a racemic or non-racemic mixture of an intermediate at some appropriate stage of the synthesis, or by resolution of the compound of formula (I). It is understood that the individual stereoisomers as well as racemic and non-racemic mixtures of stereoisomers are encompassed within the scope of the present invention.

For the sake of simplicity only one stereoisomer will be depicted by way of illustration in the Reaction Schemes. However, it is to be understood that all individual stereoisomers and racemic and non-racemic mixtures of stereoisomers are also encompassed thereby.

"Isomers" are different compounds that have the same molecular formula.

"Stereoisomers" are isomers that differ only in the way the atoms are arranged in space.

"Enantiomers" are a pair of stereoisomers that are non-superimposable mirror images of each other. Enantiomers rotate the plane of polarized light in opposite directions. The enantiomer that rotates the plane to the left is called the levo isomer, and is designated (−). The enantiomer that rotates the plane to the right is called the dextro isomer, and is designated (+).

"Diastereoisomers" are stereoisomers which are not mirror-images of each other.

"Racemic mixture" means a mixture containing equal parts of individual enantiomers. "Non-racemic mixture" is a mixture containing unequal parts of individual enantiomers.

The terms "α and β" indicate the specific stereochemical configuration of a substituent at an asymmetric carbon atom in a chemical structure as drawn. Thus "α", denoted by a broken line, indicates that the group at the position in question is below the general plane of the molecule as drawn, and "β", denoted by a bold line, indicates that the group at the position in question is above the general plane of the molecule as drawn.

The term "treatment" as used herein covers any treatment of a disease in a mammal, particularly a human, and includes:

(i) preventing the disease from occurring in a subject which may be predisposed to the disease but has not yet been diagnosed as having it;

(ii) inhibiting the disease, i.e., arresting its development; or (iii) relieving the disease, i.e., causing regression of the disease.

The numbering system used in naming the intermediates and product compounds of the present invention is illustrated below, using a compound of formula (I) as an example.

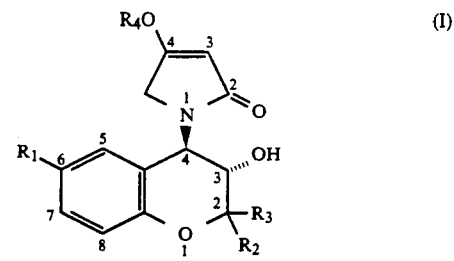

(I)

In the final product, the substituents at positions 3 and 4 on the benzopyran ring are always trans to each other.

Following are examples of how representative compounds of formula (I) are named.

A racemic compound of formula (I) wherein $R_1$ is cyano, $R_2$ and $R_3$ are both ethyl and $R_4$ is methyl is named:

6-cyano-3,4-dihydro-2,2-diethyl-trans-3-hydroxy-4-(4-methoxy-2-oxo-3-pyrrolin-1-yl)-2H-1-benzopyran.

An optically active isomer of a compound of formula (I) which is levorotatory, wherein $R_1$ is cyano, $R_2$ and $R_3$ are both methyl and $R_4$ is ethyl is named:

(−)-6-cyano-3,4-dihydro-2,2-dimethyl-trans-3-hydroxy-4-(4-ethoxy-2-oxo-3-pyrrolin-1-yl)-2H-1-benzopyran.

Preferred Embodiments

Among the family of compounds of the present invention of formula (I), a preferred group includes compounds wherein $R_1$ is cyano. Within this group a preferred subgroup includes the compounds in which $R_2$ and $R_3$ are independently methyl or ethyl, especially where they are both methyl. One preferred class within this subgroup includes compounds in which $R_4$ is alkyl, especially lower alkyl, more especially methyl or ethyl. A second preferred class within this subgroup includes compounds in which $R_4$ is alkenyl, especially lower alkenyl of 1-6 carbon atoms, more especially allyl. A third preferred class within this subgroup includes compounds in which $R_4$ is phenyl-lower-alkyl, especially benzyl.

A second preferred group includes compounds wherein $R_1$ is nitro. Within this group a preferred subgroup includes the compounds in which $R_2$ and $R_3$ are independently methyl or ethyl, especially where they are both methyl. One preferred class within this subgroup includes compounds in which $R_4$ is alkyl, especially lower alkyl, more especially methyl or ethyl.

At present the preferred compounds are:
6-cyano-3,4-dihydro-2,2-dimethyl-trans-3-hydroxy-4-(4-methoxy-2-oxo-3-pyrrolin-1-yl)-2H-1-benzopyran; and
6-cyano-3,4-dihydro-2,2-dimethyl-trans-3-hydroxy-4-(4-ethoxy-2-oxo-3-pyrrolin-1-yl)-2H-1-benzopyran.

Methods of Preparation

The compounds of formula (I) may be prepared from the intermediates of formula (2) and (3) as shown in Reaction Scheme 1 below.

REACTION SCHEME 1

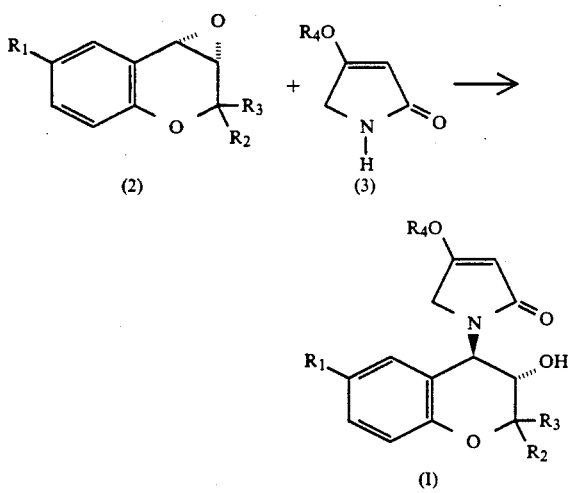

where $R_1$, $R_2$, $R_3$ and $R_4$ are as defined above.

The compound of formula (I) may be prepared by reacting the compound of formula (2) with about 1 molar equivalent of the compound of formula (3) in the presence of about 1 molar equivalent of a strong base such as potassium t-butoxide, lithium diisopropylamide, or an alkali metal hydride, for example potassium hydride, lithium hydride or preferably sodium hydride. The reaction is carried out in an aprotic solvent such as tetrahydrofuran, dimethylformamide, hexamethylphosphoramide, or preferably dimethylsulfoxide, at a temperature of about 0°-50° C., preferably about 25° C., for about 2-18 hours, preferably about 5 hours. When the reaction is substantially complete, the compound of formula (I) is isolated by conventional means and purified, preferably by chromatography followed by recrystallizing from a suitable solvent or solvent mixture such as diethylether/pentane.

An alternative preparation of the compound of formula (I) is illustrated in Reaction Scheme 2.

REACTION SCHEME 2

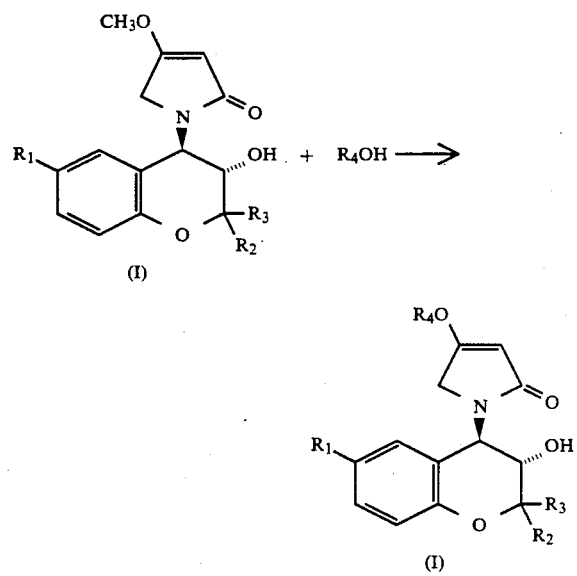

where $R_1$, $R_2$, $R_3$ and $R_4$ are as defined above.

The compound of formula (I) where $R_4$ is methyl, prepared for example as shown in Reaction Scheme 1 above, is treated with an alcohol or phenol of formula $R_4OH$ in the presence of an acid catalyst, giving a compound of formula (I) where $R_4$ corresponds to that of the $R_4OH$ employed in the reaction. Typically, a mixture of the compound of formula (I) where $R_4$ is methyl is mixed with about 1 to 10 molar equivalents, preferably about 4 molar equivalents, of the appropriate alcohol or phenol of formula $R_4OH$ and a catalytic amount, for example about 0.1 molar equivalents, of a suitable acid catalyst such as p-toluenesulfonic acid or preferably methanesulfonic acid. The mixture is heated at about 50°-150° C., preferably about 80° C., at reduced pressure, for example about 20-40 mbar, for about 1-10 hours, preferably about 3 hours. When the reaction is substantially complete, the compound of formula (I) is isolated by conventional means, for example chromatography.

Alternatively, the reaction may be carried out in the same manner as shown above, but in the presence of 3A molecular sieves, which eliminates the need for reduced pressure. The mixture is refluxed for about 1-6 hours, preferably about 2 hours, and the product isolated conventionally.

Clearly, compounds where $R_4$ is other than methyl, for example ethyl, may be used as a starting material. It is necessary, however, that the alcohol displaced is of lower boiling point than the alcohol or phenol used for its displacement.

The reaction is also useful for the preparation of optically active compounds of formula (I); for example starting with an optically active compound of formula (I) where R₄ is methyl and reacting with a compound of formula R₄OH (where R₄ is not methyl) as shown above leads to an optically active compound of formula (I) where R₄ is other than methyl.

Optical Isomers of the Compounds of Formula (I)

The optical isomers of the compound of formula (I) may be obtained in various ways. For example, reaction of a racemic mixture of a compound of formula (I) with a chiral isocyanate, for example (R)-(+)-α-methylbenzylisocyanate, gives a mixture of diastereoisomeric carbamates (formed at the 3-position by reaction with the 3-hydroxy group), which may be separated by chromatography or crystallization and converted back to the individual enantiomers of the compound of formula (I). This approach is discussed in more detail in European Patent Application 120,428. A similar method is to react a compound of formula (I) with a chiral acid derivative, for example an acid chloride, which gives a mixture of diastereoisomeric esters, which may be similarly separated and converted back to the individual enantiomers of the compound of formula (I). A typical example of a chiral acid chloride is (S)-camphanic acid chloride, the use of which is discussed in more detail in *Circulation Research*, Vol. 62, 679 (1988).

Racemic mixtures may also may be separated by chromatography on a chiral column. For example, on an α₁-acid glycoprotein column eluting with a phosphate buffer composition.

Another approach is to first resolve one of the racemic intermediates used in Reaction Schemes 1 and 2 above in the preparation of racemic compounds of formula (I). The optically active isomers of the intermediate thus obtained may then be reacted in the same manner as shown above to give optically active compounds of formula (I). A particularly suitable intermediate is the compound of formula (4), which has a 4-amino group, thus enabling diastereoisomeric salts to be formed with readily available optically active acids, which may then be separated by conventional means, preferably crystallization. The separated pure diastereomeric salts are then cleaved by standard means, such as treatment with a base, to afford the respective enantiomers of the compound of formula (4). For the sake of convenience in the discussion, the two enantiomers of (4) will be referred to as (4A) and (4B).

The latter process is clearly simpler and more convenient to carry out than those detailed above, as formation of a base salt is easier to carry out than the chemical reaction necessary to prepare chiral esters or carbamate of an alcohol, and conversion of the separated diastereoisomeric salts back to the individual isomers is easier than hydrolysis of esters or carbamates to the free alcohol. In particular, care must be taken in the hydrolysis of chiral esters or carbamates, in that use of a strong base may lead to racemization of the optically active compound.

In addition, separation of optical isomers at an earlier stage of the synthesis is generally preferred to separation of optical isomers of the final product, especially in the case where one of the isomers is inactive, as it is more convenient and economical to remove the unwanted isomer before it is reacted with expensive reactants. Yet another consideration is that for compounds of formula (4), the optical isomers of formula (4A) and (4B) can be reacted with various compounds of formula (5) to give a series of optically active compounds of formula (I), thus eliminating the need to resolve a large number of compounds.

Exemplary of optically active acids are the optically active forms of camphor-10-sulfonic acid, 2-bromo-camphor-10-sulfonic acid, camphoric acid, menthosyacetic acid, tartaric acid, malic acid, mandelic acid, diacetyltartaric acid, pyrrolidine-5-carboxylic acid, abietic acid, aspartic acid, deoxycholic acid, di-p-toluoyltartaric acid, glutamic acid, lactic acid, pyroglutamic acid, and the like. The preferred optically active acid is dibenzoyltartaric acid in the D or L form. Typically the compound of formula (4) is reacted with about 1 molar equivalent of an optically active acid, for example dibenzoyl-L-tartaric acid. The reaction is carried out in a suitable solvent such as methanol, propanol, 2-methoxyethanol, dimethylformamide, acetonitrile and the like, preferably ethanol, at a temperature of about 20°-100° C., preferably about 70° C., for about 10 minutes to 2 hours, preferably about 30 minutes. The reaction mixture is then allowed to cool to about 0°-40° C., preferably about 25° C., for about 1-8 hours, preferably about 3 hours. The precipitated salt thus obtained is treated with base conventionally to give one enantiomer of formula (4A) or (4B).

The opposite enantiomer may be obtained in a similar manner as shown above, starting with the optically active acid used above but of opposite rotation, for example dibenzoyl-D-tartaric acid. Alternatively, the salt remaining dissolved in the filtrate (from which the precipitated salt of the first isomer is filtered) may be converted to the free amine as shown above and treated with the optically active acid of opposite rotation, for example dibenzoyl-D-tartaric acid, giving the other diastereomeric salt from which the opposite enantiomer is obtained.

The individual optical isomers of formula (4A) and (4B) are then converted to the optically active compounds of formula (I) by reaction with a compound of formula (5) where X and R are as defined below, to give an intermediate of formula (6), which is cyclized to (I) as shown in Reaction Scheme 3.

REACTION SCHEME 3

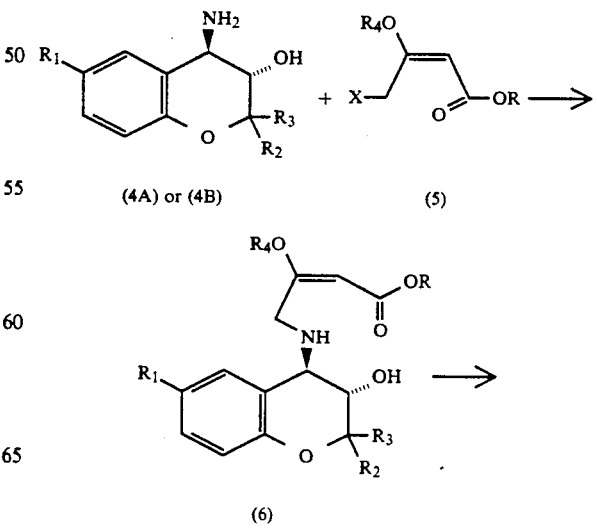

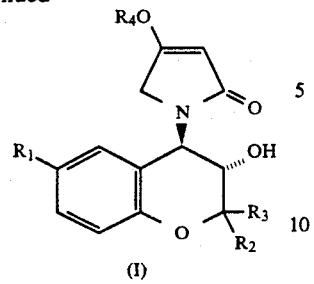

(I)

is chloro, bromo or iodo and R is lower alkyl, preferably methyl where $R_4$ is methyl, or otherwise ethyl.

The compound of formula (I) is prepared by first reacting the chiral compound of formula (4A) or (4B) with about 1-1.5 molar equivalents, preferably about 1.3 molar equivalents, of the compound of formula (5) where X and R are as defined above, in the presence of about 1-1.5 molar equivalents, preferably about 2 molar equivalents, of a base such as a tertiary amine, for example pyridine, N,N-dimethylaniline, diisopropylethylamine or preferably triethylamine, or an inorganic base such as sodium carbonate, calcium carbonate, sodium hydroxide and the like, preferably potassium carbonate, and about 0.5-1.5 molar equivalents, preferably about 1 molar equivalent, of an alkaline metal iodide, preferably potassium iodide. The reaction is carried out in a protic solvent such as methanol, ethanol, 2-methoxyethanol and the like, preferably isopropanol, at a temperature of about 50°-100° C., preferably at reflux temperature, for about 30 minutes to 8 hours, preferably about 3 hours. When the reaction is substantially complete, the compound of formula (6) is isolated by conventional means and purified, preferably by chromatography. The compound of formula (6) is then cyclized, preferably by heating in an inert solvent, preferably xylene, at a temperature of about 80°-140° C., preferably at reflux temperature, for about 10-48 hours, preferably about 15 hours. When the reaction is substantially complete, the optically active compound of formula (I) is isolated by conventional means and purified, preferably by chromatography.

The process detailed in Reaction Scheme 3 can also of course conveniently be used for the preparation of racemic mixtures of the compound of formula (I), starting with the appropriate racemic compound of formula (4) and proceeding through a racemic intermediate of formula (6).

Preparation of Starting Materials

The compounds of formula (2) are well known in the art. See for example U.S. Pat. No. 4,062,870, the disclosure of which, and all other documents referred to throughout the specification, are herein incorporated by reference. For example, the compound of formula (2) wherein $R_1$ is cyano and $R_2$ and $R_3$ are both methyl is prepared by reacting 4-cyanophenol with 3-methyl-3-chlorobutyne, cyclizing the product to 6-cyanochromene, forming the trans 3,4-bromhydrin by reaction with N-bromosuccinimide and treating this bromohydrin with base to give the desired epoxide of formula (2). This reaction scheme is set forth in more detail in European Patent Application No. 093,535.

The compounds of formula (3) are known in the art. For example, the compound of formula (3) where $R_4$ is methyl is disclosed in J.A.C.S., 85, 1430 (1963), where $R_4$ is methyl or ethyl in European Patent Application No. 216,324, and where $R_4$ is benzyl in European Patent Application No. 252,363.

The compounds of formula (3) can also be prepared as shown in Reaction Scheme 4.

REACTION SCHEME 4

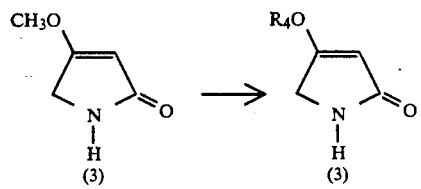

The compound of formula (3) where $R_4$ is methyl, upon treatment with an alcohol or phenol of formula $R_4OH$ in the presence of an acid catalyst, gives a compound of formula (3) where $R_4$ is other than methyl. Typically, a mixture of the compound of formula (3) where $R_4$ is methyl is mixed with about 1 to 10 molar equivalents, preferably about 2 molar equivalents, of the appropriate alcohol or phenol of formula $R_4OH$ and a catalytic amount, for example about 0.1 molar equivalents, of a suitable acid catalyst such as p-toluenesulfonic acid or preferably methanesulfonic acid. The mixture is heated at about 50°-150° C., preferably about 100° C., at reduced pressure, for example about 40 mbar, for about 1-10 hours, preferably about 3 hours. When the reaction is substantially complete, the compound of formula (3) is isolated by conventional means.

Alternatively, the reaction may be carried out in the same manner as shown above, but in the presence of 3A molecular sieves, which eliminates the need for reduced pressure. The mixture is refluxed for about 1-6 hours, preferably about 2 hours, and the product isolated conventionally.

Clearly, compounds other than the compound of formula (3) where $R_4$ is methyl may be used as a starting material. It is necessary, however, that the alcohol displaced is of lower boiling point than the alcohol or phenol used for its displacement.

The compound of formula (4) is known in the art. See, for example, U.S. Pat. No. 4,251,537, or European Patent Application No. 093,535.

The compounds of formula (5) are known in the art. See for example European Patent Application No. 216,324.

In summary, the compounds of the present invention are made by the procedures outlined below:

1. A process for preparing compounds of the formula (I) wherein:

$R_1$ is cyano or nitro;

$R_2$ and $R_3$ are independently hydrogen or lower alkyl; and $R_4$ is alkyl; alkenyl; phenyl or phenyl-lower-alkyl in which any phenyl group may be optionally substituted with one or two substituents chosen from lower alkyl, lower alkoxy, halo, trifluoromethyl and hydroxy; $(CH_2)_mOR_2$ or $-(CH_2)_mN(R_2)_2$; wherein m is an integer of 1-5 and $R_2$ is as defined above; comprises:

reacting a compound of the formula

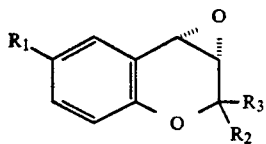

(2)

wherein $R_1$, $R_2$ and $R_3$ are as defined above, with a compound of the formula

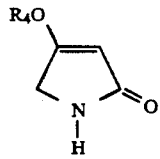

(3)

wherein $R_4$ is as defined above.

2. Alternatively, a process for preparing compounds of formula (I) above comprises:
cyclizing a compound of the formula

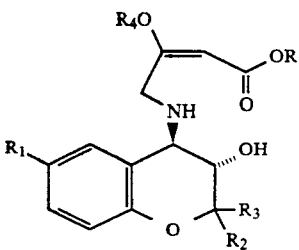

(6)

wherein $R_1$, $R_2$, $R_3$ and $R_4$ are as defined above and R is lower alkyl, optionally in the presence of an inert solvent.

3. Alternatively, a process for preparing compounds of formula (I) above comprises:
reacting a compound of the formula

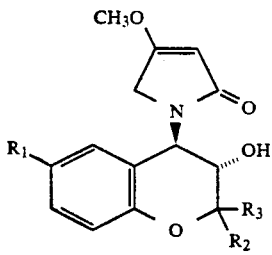

wherein $R_1$, $R_2$ and $R_3$ are as defined above, with a compound of the formula $R_4OH$ in the presence of an acid catalyst, optionally in the presence of molecular sieves.

Utility and administration

The compounds of the present invention exhibit smooth muscle relaxant biological activities, and are thus used in the treatment of mammals where the use of smooth muscle relaxants is indicated. The compounds of formula (I) are particularly useful as antihypertensive agents to reduce blood pressure in mammals, including man.

Other physiological uses of the novel compounds of formula (I) include, for example, treatment of congestive heart failure, angina, smooth muscle spasm, in particular cerebro-vasospasm, cardiac arrhythmia, stroke, dysmenorrhea, renal failure, peripheral vascular occlusive disease, unstable bladder and urinary retention, nocturnal asthma, and gastrointestinal disorders, in particular irritable bowel syndrome. Other indications include treatment of baldness.

In applying the compounds of this invention to treatment of the above conditions, any pharmaceutically acceptable mode of administration can be used, either alone or in combination with other pharmaceutically acceptable excipients, including solid, semi-solid liquid or aerosol dosage forms, such as, for example, tablets, pills, capsules, powders, liquids, suspensions, aerosols or the like, preferably in unit dosage forms suitable for single adminstration of precise dosages, or in sustained or controlled release dosage forms for the prolonged administration of the compound at a predetermined rate. The compositions will typically include a conventional pharmaceutical carrier or excipient and an active compound of formula (I) or the pharmaceutically accetable salts thereof and, in addition, may include other medicinal agents, pharmaceutical agents, carriers, adjuvants, etc.

The amount of active compound administered will, of course, be dependent on the subject and disease state being treated, the severity of the affliction, the manner of administration and the judgment of the prescribing physician. However, an effective dosage is in the range of 0.001 mg to about 10 mg/kg. For an average 70 kg human, this would amount to 0.07-700 mg per day, or preferably 0.7-70 mg/day.

For solid compositions, conventional non-toxic solid carriers include, for example, pharmaceutical grades of mannitol, lactose, starch, magnesium stearate, sodium saccharin, talcum, cellulose, glucose, sucrose, magnesium carbonate, and the like may be used. Liquid pharmaceutically administerable compositions can, for example, be prepared by dissolving, dispersing, etc. an active compound as defined above and optional pharmaceutical adjuvants in a carrier, such as, for example, water, saline, aqueous dextrose, glycerol, ethanol, and the like, to thereby form a solution or suspension. If desired, the pharmaceutical composition to be administered may also contain minor amounts of nontoxic auxiliary substances such as wetting or emulsifying agents, pH buffering agents and the like, for example, sodium acetate, sorbitan monolaurate, triethanolamine sodium acetate, sorbitan monolaurate, triethanolamine oleate, etc. Actual methods of preparing such dosage forms are known, or will be apparent, to those skilled in this art; for example, see *Remington's Pharmaceutical Sciences*, Mack Publishing Company, Easton, Pa., 15th Edition, 1975. The composition or formulation to be administered will, in any event, contain a quantity of the active compound(s) in an amount effective to alleviate the symptoms of the subject being treated.

Dosage forms or compositions containing active ingredient (compounds of formula (I)) in the range of 0.1 to 95% with the balance made up from non-toxic carrier may be prepared.

For oral administration, a pharmaceutically acceptable non-toxic composition is formed by the incorporation of any of the normally employed excipients, such as, for example pharmaceutical grades of mannitol, lactose, starch, magnesium stearate, sodium saccharin, talcum, cellulose, glucose, sucrose, magnesium, carbonate, and the like. Such compositions take the form of solutions, suspensions, tablets, pills, capsules, powders, sustained release formulations and the like. Such compositions may contain 0.01%–95% active ingredient, preferably 0.1–50%.

Particularly preferred oral formulations of the compounds of formula (I) are formulations in which the compound is dissolved in a propylene glycol diester of a short-chain fatty acid or in a cyclic carbonate diester, such as propylene carbonate. For a solid dosage form, the solution, e.g. in propylene carbonate, is preferably encapsulated in a soft-shelled gelatine capsule. Such diester solutions, and the preparation and encapsulation thereof, are disclosed in U.S. Pat. Nos. 4,328,245; 4,409,239; and 4,410,545. For a liquid dosage form, the solution, e.g. in propylene carbonate, may be diluted with a sufficient quantity of a pharmaceutically-acceptable liquid carrier, e.g. water, to be easily measured for administration.

Other useful formulations include those set forth in U.S. Pat. Nos. Re. 28,819 and 4,358,603.

The formulation can be administered in a single unit dosage form for continuous treatment or in a single unit dosage form ad libitum when relief of symptoms is specifically required.

Parenteral administration is generally characterized by injection, either subcutaneously, intramuscularly or intravenously. Injectables can be prepared in conventional forms, either as liquid solutions or suspensions, solid forms suitable for solution or suspension in liquid prior to injection, or as emulsions. Suitable excipients are, for example, water, saline, dextrose, glycerol, ethanol or the like. In addition, if desired, the pharmaceutical compositions to be administered may also contain minor amounts of non-toxic auxiliary substances such as wetting or emulsifying agents, pH buffering agents and the like, such as for example, sodium acetate, sorbitan monolaurate, triethanolamine oleate, etc.

A more recently devised approach for parenteral administration employs the implantation of a slow-release or sustained-release system, such that a constant level of dosage is maintained. See, e.g., U.S. Pat. No. 3,710,795.

The percentage of active compound contained in such parental compositions is highly dependent on the specific nature thereof, as well as the activity of the compound and the needs of the subject. However, percentages of active ingredient of 0.01% to 10% in solution are employable, and will be higher if the composition is a solid which will be subsequently diluted to the above percentages. Preferably the composition will comprise 0.2–2% of the active agent in solution.

The following preparations and examples illustrate the invention, but are not intended to limit its scope.

PREPARATION 1

Preparation of
6-cyano-3,4-dihydro-2,2-dimethyl-3,4-epoxy-2H-1-benzopyran and Related Compounds of Formula (2)

A. 4-Cyanophenol (201.3 g), sodium hydroxide (101.4 g), 40% benzyltrimethylammonium hydroxide in methanol (353 g) and 3-methyl-3-chlorobutyne (260 g) were stirred in a mixture of water (1500 ml) and dichloromethane (1500 ml) for 5 days at room temperature. After separation the organic layer was washed with 10% sodium hydroxide solution (400 ml) and dried over sodium sulphate. The solvent was removed under reduced pressure, leaving a viscous liquid. This liquid (225.6 g) was heated in o-dichlorobenzene (450 ml) at reflux temperature for 3 hours under nitrogen. The solvent was removed under reduced pressure (70° C. at 3 mm of Hg), leaving a brown oil (225 g) identified as 6-cyanochromene.

To a solution of the 6-cyanochromene (225 g) in dimethyl sulphoxide (2 l) containing water (22 ml) was added N-bromosuccinimide (433.6 g) with vigorous stirring and cooling to 10° C. After 1 hour at room temperature the mixture was diluted with water and extracted with ethyl acetate to give a mixture which was refluxed in acetone (4 l) and water (1.3 l) for 5 hours to hydrolyse the small amount of 3,4-dibromide present. The acetone was removed under reduced pressure, leaving a precipitate in water. After filtration, the precipitate was dissolved in diethylether and precipitated with pentane, to give 145 g of trans-3-bromo-4-hydroxy-6-cyano-3,4-dihydro-2,2-dimethyl-2H-1-benzopyran as white crystals, m.p. 230° C.

Removal of the solvent from the filtrate and chromatography of the residue on silica gel, eluting with methylene chloride, gave an additional 68.5 g of the bromohydrin, m.p. 230° C.

The bromohydrin (213.5 g) was stirred with sodium hydroxide (45.4 g) in a mixture of water (2.2 l) and dioxane (1.76 l) for 2 hours at room temperature. The dioxane was removed under reduced pressure and the resulting precipitate filtered off. The precipitate was then dissolved in methylene chloride, dried over sodium sulfate and chromatographed on silica gel, eluting with methylene chloride, to give 6-cyano-3,4-dihydro-2,2-dimethyl-3,4-epoxy-2H-1-benzopyran as white crystals, m.p. 108° C.

B. Similarly, optionally replacing 4-cyanophenol with 4-nitrophenol, and optionally replacing 3-methyl-3-chlorobutyne with a propyne substituted in the 3-position with the appropriate definitions of $R_2$ and $R_3$, the following compounds of formula (2) are prepared:

6-cyano-3,4-dihydro-2-methyl-3,4-epoxy-2H-1-benzopyran;

6-cyano-3,4-dihydro-2-ethyl-3,4-epoxy-2H-1-benzopyran;

6-cyano-3,4-dihydro-2-n-butyl-3,4-epoxy-2H-1-benzopyran;

6-cyano-3,4-dihydro-2-methyl-2-ethyl-3,4-epoxy-2H-1-benzopyran;

6-cyano-3,4-dihydro-2,2-diethyl-3,4-epoxy-2H-1-benzopyran;

6-cyano-3,4-dihydro-2,2-di-n-butyl-3,4-epoxy-2H-1-benzopyran;

6-nitro-3,4-dihydro-2,2-dimethyl-3,4-epoxy-2H-1-benzopyran;

6-nitro-3,4-dihydro-2-methyl-3,4-epoxy-2H-1-benzopyran;

6-nitro-3,4-dihydro-2-ethyl-3,4-epoxy-2H-1-benzopyran;

6-nitro-3,4-dihydro-2-n-butyl-3,4-epoxy-2H-1-benzopyran;

6-nitro-3,4-dihydro-2-methyl-2-ethyl-3,4-epoxy-2H-1-benzopyran;

6-nitro-3,4-dihydro-2,2-diethyl-3,4-epoxy-2H-1-benzopyran; and 6-nitro-3,4-dihydro-2,2-di-n-butyl-3,4-epoxy-2H-1-benzopyran.

PREPARATION 2

Preparation of 4-methoxy-3-pyrrolin-2-one and Related Compounds of Formula (3)

A. A mixture of methyl 4-chloroacetoacetate (96.5 g) and trimethyl orthoformate (340.2 g) was stirred under argon with 96.5 g of Amberlyst-15 ion exchange resin. The temperature was raised to 40° C. and stirring continued for 5 hours. The resin was filtered off and the filtrate distilled under vacuum (15 mm). The distillate was mixed with 3.2 g of p-toluenesulfonic acid and heated at 150° C. until no more methanol distilled off. Distillation of the residue under vacuum gave 4-chloro-3-methoxy-2-E-butenoic acid, methyl ester, b.p. 75° C. (3 mm Hg).

The 4-chloro-3-methoxy-2-E-butenoic acid, methyl ester thus obtained (84.42 g) was stirred with 210 ml of 28% aqueous ammonia solution under a reflux condenser at 80° C. for 2 hours. The mixture was then cooled to room temperature and extracted with methylene chloride. The extract was dried over sodium sulfate, filtered and solvent removed from the filtrate under reduced pressure. The residue was triturated with diethyl ether, giving 40,6 g of 4-methoxy-3-pyrrolin-2-one, m.p. 132° C.

B. Similarly, replacing trimethyl orthoformate with triethyl orthoformate, 4-ethoxy-3-pyrrolin-2-one was prepared, m.p. 148° C.

PREPARATION 3

Preparation of 4-octyloxy-3-pyrrolin-2-one and Related Compounds of Formula (3)

A. A mixture of 4-methoxy-3-pyrrolin-2-one (3 g), 1-octanol (7.4 ml) and methanesulfonic acid (0.2 g) were heated at 100° C. for 2 hours under reduced pressure (40 mbars). The product was chromatographed on silica gel, eluting with 2% methanol in methylene chloride, to give 4-octyloxy-3-pyrrolin-2-one.

B. Similarly, replacing 1-octanol with the appropriate alcohol of the formula R$_4$OH, the following compounds of formula (3) were prepared:
4-benzyloxy-3-pyrrolin-2-one; and
4-(3-bromopropoxy)-3-pyrrolin-2-one.

Alternative Procedure

C. A mixture of 4-methoxy-3-pyrrolin-2-one (3 g), 1-propanol (3.5 ml) and methanesulfonic acid (0.2 g) was refluxed for 2 hours in the presence of 3A molecular sieves. Solvent was removed from the mixture, and the residue chromatographed on silica gel, eluting with 2% methanol in methylene chloride, to give 4-n-propoxy-3-pyrrolin-2-one.

D. Similarly, replacing 1-propanol with the appropriate alcohol of the formula R$_4$OH, the following compounds of formula (3) were prepared:
4-ethoxy-3-pyrrolin-2-one;
4-n-butoxy-3-pyrrolin-2-one;
4-iso-butoxy-3-pyrrolin-2-one; and
4-allyloxy-3-pyrrolin-2-one.

E. Similarly, replacing 1-octanol with the appropriate alcohol or phenol of the formula R$_4$OH, the following compounds of formula (3) are prepared:
4-iso-propoxy-3-pyrrolin-2-one;
4-t-butoxy-3-pyrrolin-2-one;
4-n-pentyloxy-3-pyrrolin-2-one;
4-n-hexyloxy-3-pyrrolin-2-one;
4-(5-methylhexyloxy)-3-pyrrolin-2-one;
4-dodecyloxy-3-pyrrolin-2-one;
4-(but-3-en-1-yloxy)-3-pyrrolin-2-one;
4-phenoxy-3-pyrrolin-2-one;
4-(2-methylphenoxy)-3-pyrrolin-2-one; and
4-(1-phenylethoxy)-3-pyrrolin-2-one.

PREPARATION 4

Resolution of trans-4-amino-6-cyano-3,4-dihydro-3-hydroxy-2,2-dimethyl-2H-1-benzopyran and Related Compounds of Formula (4)

A. A mixture of racemic 6-cyano-3-4-dihydro-2,2-dimethyl-trans-3-hydroxy-4-amino-2H-1-benzopyran (14 g) and dibenzoyl-L-tartaric acid (24 g) was heated at 70° C. in ethanol (50 ml) with stirring for 30 minutes, then stood for 3 hours at room temperature without stirring. The precipitate was filtered off and dried to give 15.88 g of salt. This crude salt was triturated in hot ethanol (100 ml) to give 12.67 g of the dibenzoyl-L-tartaric acid salt of 6-cyano-3,4-dihydro-2,2-dimethyl-trans-3-hydroxy-4-amino-2H-1-benzopyran, mp 230° C., $[\alpha]_D^{25} = -4.06$ (c=0.49, DMF).

The salt (7.5 g) was treated with a mixture of water (100 ml) and 10N sodium hydroxide (5 ml), and the mixture extracted with diethyl ether (200 ml), giving 2.7 g of the (+) isomer form of 6-cyano-3,4-dihydro-2,2-dimethyl-trans-3-hydroxy-4-amino-2H-1-benzopyran as an amorphous solid, $[\alpha]_D^{25} = +71.97$ (c=1.0 Ethanol).

The mother liquor obtained during the first precipitation of the crude salt was treated with a mixture of water (300 ml) and 10N sodium hydroxide (15 ml), and extracted with diethyl ether (2×300 ml), giving 6-cyano-3,4-dihydro-2,2-dimethyl-trans-3-hydroxy-4-amino-2H-1-benzopyran (7.83 g) enriched in the (−) isomer form. This product was stirred at 70° C. with dibenzoyl-D-tartaric acid (12 g) in ethanol (50 ml) for 30 minutes then stood for 21 hours at room temperature without stirring. The precipitate thus formed was filtered and dried giving 14.28 g of the dibenzoyl-D-tartaric acid salt of 6-cyano-3,4-dihydro-2,2-dimethyl-trans-3-hydroxy-4-amino-2H-1-benzopyran, mp 230° C., $[\alpha]_D^{25} = +3.86$ (c=0.47, DMF).

After treating the salt (7.5 g) with sodium hydroxide as described above, 2.7 g of the (−) isomer form of 6-cyano-3,4-dihydro-2,2-dimethyl-trans-3-hydroxy-4-amino-2H-1-benzopyran was obtained as an amorphous solid, $[\alpha]_D^{25} = -72.32$ (c=1.13 Ethanol).

B. Similarly, replacing 6-cyano-3-4-dihydro-2,2-dimethyl-trans-3-hydroxy-4-amino-2H-1-benzopyran with the appropriate compound of formula (4), the (+) and (−) optical isomers of the following compounds of formula (4) are separated:
6-cyano-3,4-dihydro-2-methyl-trans-3-hydroxy-4-amino-2H-1-benzopyran;
6-cyano-3,4-dihydro-2-ethyl-trans-3-hydroxy-4-amino-2H-1-benzopyran;
6-cyano-3,4-dihydro-2-n-butyl-trans-3-hydroxy-4-amino-2H-1-benzopyran;
6-cyano-3,4-dihydro-2-methyl-2-ethyl-trans-3-hydroxy-4-amino-2H-1-benzopyran;
6-cyano-3,4-dihydro-2,2-diethyl-trans-3-hydroxy-4-amino-2H-1-benzopyran;
6-cyano-3,4-dihydro-2,2-di-n-butyl-trans-3-hydroxy-4-amino-2H-1-benzopyran;
6-nitro-3,4-dihydro-2-methyl-trans-3-hydroxy-4-amino-2H-1-benzopyran;

6-nitro-3,4-dihydro-2-ethyl-trans-3-hydroxy-4-amino-2H-1-benzopyran;
6-nitro-3,4-dihydro-2-n-butyl-trans-3-hydroxy-4-amino-2H-1-benzopyran;
6-nitro-3,4-dihydro-2-methyl-2-ethyl-trans-3-hydroxy-4-amino-2H-1-benzopyran;
6-nitro-3,4-dihydro-2,2-dimethyl-trans-3-hydroxy-4-amino-2H-1-benzopyran;
6-nitro-3,4-dihydro-2,2-diethyl-trans-3-hydroxy-4-amino-2H-1-benzopyran; and
6-nitro-3,4-dihydro-2,2-di-n-butyl-trans-3-hydroxy-4-amino-2H-1-benzopyran.

PREPARATION 5

Preparation of
6-cyano-3,4-dihydro-2,2-dimethyl-trans-3-hydroxy-4-(2-methoxy-3-carbonylmethoxy-2-E-propen-1-yl)amino-2H-1-benzopyran and Related Compounds of Formula (6)

A. A mixture of 6-cyano-3,4-dihydro-2,2-dimethyl-trans-3-hydroxy-4-amino-2H-1-benzopyran (4.7 g), 4-chloro-3-methoxy-2-E-butenoic acid, methyl ester (3.55 g), potassium carbonate (5.95 g) and sodium iodide (3.2 g) was refluxed for 3 hours in isopropanol. After cooling the mixture was filtered and solvent removed from the filtrate under reduced pressure, to give 1.1 g of 6-cyano-3,4-dihydro-2,2-dimethyl-trans-3-hydroxy-4-(2-methoxy-3-carbonylmethoxy-2-E-propen-1-yl)amino-2H-1-benzopyran, a compound of formula (6). The compound was used in the next reaction (Example 3) with no further purification.

B. Similarly, replacing 4-chloro-3-methoxy-2-E-butenoic acid, methyl ester with 4-chloro-3-ethoxy-2-E-butenoic acid, ethyl ester, the following racemic compound of formula (6) was prepared:
6-cyano-3,4-dihydro-2,2-dimethyl-trans-3-hydroxy-4-(2-ethoxy-3-carbonylethoxy-2-E-propen-1-yl)amino-2H-1-benzopyran.

C. Similarly, replacing 6-cyano-3,4-dihydro-2,2-dimethyl-trans-3-hydroxy-4-amino-2H-1-benzopyran with its (−) or (+) optically active isomer and replacing 4-chloro-3-methoxy-2-E-butenoic acid, methyl ester with 4-chloro-3-ethoxy-2-E-butenoic acid, ethyl ester, the following optically active compounds of formula (6) were prepared, respectively:
(−)-6-cyano-3,4-dihydro-2,2-dimethyl-trans-3-hydroxy-4-(2-ethoxy-3-carbonylethoxy-2-E-propen-1-yl)amino-2H-1-benzopyran; and
(+)-6-cyano-3,4-dihydro-2,2-dimethyl-trans-3-hydroxy-4-(2-ethoxy-3-carbonylethoxy-2-E-propen-1-yl)amino-2H-1-benzopyran.

D. Similarly, optionally replacing 6-cyano-3,4-dihydro-2,2-dimethyl-trans-3-hydroxy-4-amino-2H-1-benzopyran with the appropriate optically active or racemic compound of formula (4), and optionally replacing 4-chloro-3-methoxy-2-E-butenoic acid, methyl ester with the appropriate compound of formula (5), the following compounds of formula (6) are prepared as the (−) or (+) optical isomer or as a racemic mixture:
6-cyano-3,4-dihydro-2,2-dimethyl-trans-3-hydroxy-4-(2-methoxy-3-carbonylmethoxy-2-E-propen-1-yl)amino-2H-1-benzopyran;
6-cyano-3,4-dihydro-2,2-dimethyl-trans-3-hydroxy-4-(2-benzyloxy-3-carbonylethoxy-2-E-propen-1-yl)amino-2H-1-benzopyran;
6-cyano-3,4-dihydro-2,2-dimethyl-trans-3-hydroxy-4-(2-isobutoxy-3-carbonylethoxy-2-E-propen-1-yl)amino-2H-1-benzopyran;
6-cyano-3,4-dihydro-2,2-dimethyl-trans-3-hydroxy-4-(2-octyloxy-3-carbonylethoxy-2-E-propen-1-yl)amino-2H-1-benzopyran;
6-cyano-3,4-dihydro-2,2-dimethyl-trans-3-hydroxy-4-(2-n-propoxy-3-carbonylethoxy-2-E-propen-1-yl)amino-2H-1-benzopyran;
6-cyano-3,4-dihydro-2,2-dimethyl-trans-3-hydroxy-4-(2-i-propoxy-3-carbonylethoxy-2-E-propen-1-yl)amino-2H-1-benzopyran;
6-cyano-3,4-dihydro-2,2-dimethyl-trans-3-hydroxy-4-(2-n-butoxy-3-carbonylethoxy-2-E-propen-1-yl)amino-2H-1-benzopyran;
6-cyano-3,4-dihydro-2,2-dimethyl-trans-3-hydroxy-4-(2-t-butoxy-3-carbonylethoxy-2-E-propen-1-yl)amino-2H-1-benzopyran;
6-cyano-3,4-dihydro-2,2-dimethyl-trans-3-hydroxy-4-(2-n-hexyloxy-3-carbonylethoxy-2-E-propen-1-yl)amino-2H-1-benzopyran;
6-cyano-3,4-dihydro-2,2-dimethyl-trans-3-hydroxy-4-(2-dodecyloxy-3-carbonylethoxy-2-E-propen-1-yl)amino-2H-1-benzopyran;
6-cyano-3,4-dihydro-2-methyl-trans-3-hydroxy-4-(2-ethoxy-3-carbonylethoxy-2-E-propen-1-yl)amino-2H-1-benzopyran;
6-cyano-3,4-dihydro-2-ethyl-trans-3-hydroxy-4-(2-ethoxy-3-carbonylethoxy-2-E-propen-1-yl)amino-2H-1-benzopyran;
6-cyano-3,4-dihydro-2-n-butyl-trans-3-hydroxy-4-(2-ethoxy-3-carbonylethoxy-2-E-propen-1-yl)amino-2H-1-benzopyran;
6-cyano-3,4-dihydro-2-methyl-2-ethyl-trans-3-hydroxy-4-(2-ethoxy-3-carbonylethoxy-2-E-propen-1-yl)amino-2H-1-benzopyran;
6-cyano-3,4-dihydro-2,2-diethyl-trans-3-hydroxy-4-(2-ethoxy-3-carbonylethoxy-2-E-propen-1-yl)amino-2H-1-benzopyran;
6-cyano-3,4-dihydro-2,2-diethyl-trans-3-hydroxy-4-(2-methoxy-3-carbonylmethoxy-2-E-propen-1-yl)amino-2H-1-benzopyran;
6-cyano-3,4-dihydro-2,2-diethyl-trans-3-hydroxy-4-(2-n-hexyloxy-3-carbonylethoxy-2-E-propen-1-yl)amino-2H-1-benzopyran;
6-cyano-3,4-dihydro-2,2-di-n-butyl-trans-3-hydroxy-4-(2-ethoxy-3-carbonylethoxy-2-E-propen-1-yl)amino-2H-1-benzopyran;
6-cyano-3,4-dihydro-2,2-dimethyl-trans-3-hydroxy-4-(2-allyloxy-3-carbonylethoxy-2-E-propen-1-yl)amino-2H-1-benzopyran;
6-cyano-3,4-dihydro-2,2-dimethyl-trans-3-hydroxy-4-[2-(but-3-en-1-yl)oxy-3-carbonylethoxy-2-E-propen-1-yl]-amino-2H-1-benzopyran;
6-cyano-3,4-dihydro-2,2-dimethyl-trans-3-hydroxy-4-(phenoxy-3-carbonylethoxy-2-E-propen-1-yl)amino-2H-1-benzopyran;
6-cyano-3,4-dihydro-2,2-dimethyl-trans-3-hydroxy-4-[(1-phenylethoxy)-3-carbonylethoxy-2-E-propen-1-yl]-amino-2H-1-benzopyran;
6-nitro-3,4-dihydro-2,2-dimethyl-trans-3-hydroxy-4-(2-ethoxy-3-carbonylethoxy-2-E-propen-1-yl)amino-2H-1-benzopyran;
6-nitro-3,4-dihydro-2,2-dimethyl-trans-3-hydroxy-4-(2-methoxy-3-carbonylethoxy-2-E-propen-1-yl)amino-2H-1-benzopyran;

6-nitro-3,4-dihydro-2,2-dimethyl-trans-3-hydroxy-4-(2-benzyloxy-3-carbonylethoxy-2-E-propen-1-yl)amino-2H-1-benzopyran;

6-nitro-3,4-dihydro-2,2-dimethyl-trans-3-hydroxy-4-(2-isobutoxy-3-carbonylethoxy-2-E-propen-1-yl)amino-2H-1-benzopyran;

6-nitro-3,4-dihydro-2,2-dimethyl-trans-3-hydroxy-4-(2-octyloxy-3-carbonylethoxy-2-E-propen-1-yl)amino-2H-1-benzopyran;

6-nitro-3,4-dihydro-2,2-dimethyl-trans-3-hydroxy-4-(2-n-propoxy-3-carbonylethoxy-2-E-propen-1-yl)amino-2H-1-benzopyran;

6-nitro-3,4-dihydro-2,2-dimethyl-trans-3-hydroxy-4-(2-i-propoxy-3-carbonylethoxy-2-E-propen-1-yl)amino-2H-1-benzopyran;

6-nitro-3,4-dihydro-2,2-dimethyl-trans-3-hydroxy-4-(2-n-butoxy-3-carbonylethoxy-2-E-propen-1-yl)amino-2H-1-benzopyran; and 6-nitro-3,4-dihydro-2,2-dimethyl-trans-3-hydroxy-4-(2-t-butoxy-3-carbonylethoxy-2-E-propen-1-yl)amino-2H-1-benzopyran.

6-nitro-3,4-dihydro-2,2-dimethyl-trans-3-hydroxy-4-(2-n-hexyloxy-3-carbonylethoxy-2-E-propen-1-yl)amino-2H-1-benzopyran;

6-nitro-3,4-dihydro-2,2-dimethyl-trans-3-hydroxy-4-(2-dodecyloxy-3-carbonylethoxy-2-E-propen-1-yl)amino-2H-1-benzopyran;

6-nitro-3,4-dihydro-2-methyl-trans-3-hydroxy-4-(2-ethoxy-3-carbonylethoxy-2-E-propen-1-yl)amino-2H-1-benzopyran;

6-nitro-3,4-dihydro-2-ethyl-trans-3-hydroxy-4-(2-ethoxy-3-carbonylethoxy-2-E-propen-1-yl)amino-2H-1-benzopyran;

6-nitro-3,4-dihydro-2-n-butyl-trans-3-hydroxy-4-(2-ethoxy-3-carbonylethoxy-2-E-propen-1-yl)amino-2H-1-benzopyran;

6-nitro-3,4-dihydro-2-methyl-2-ethyl-trans-3-hydroxy-4-(2-ethoxy-3-carbonylethoxy-2-E-propen-1-yl)amino-2H-1-benzopyran;

6-nitro-3,4-dihydro-2,2-diethyl-trans-3-hydroxy-4-(2-ethoxy-3-carbonylethoxy-2-E-propen-1-yl)amino-2H-1-benzopyran;

6-nitro-3,4-dihydro-2,2-diethyl-trans-3-hydroxy-4-(2-methoxy-3-carbonylmethoxy-2-E-propen-1-yl)amino-2H-1-benzopyran;

6-nitro-3,4-dihydro-2,2-diethyl-trans-3-hydroxy-4-(2-n-hexyloxy-3-carbonylethoxy-2-E-propen-1-yl)amino-2H-1-benzopyran;

6-nitro-3,4-dihydro-2,2-di-n-butyl-trans-3-hydroxy-4-(2-ethoxy-3-carbonylethoxy-2-E-propen-1-yl)amino-2H-1-benzopyran;

6-nitro-3,4-dihydro-2,2-dimethyl-trans-3-hydroxy-4-(2-allyloxy-3-carbonylethoxy-2-E-propen-1-yl)amino-2H-1-benzopyran;

6-nitro-3,4-dihydro-2,2-dimethyl-trans-3-hydroxy-4-[2-(but-3-en-1-yl)oxy-3-carbonylethoxy-2-E-propen-1-yl]-amino-2H-1-benzopyran;

6-nitro-3,4-dihydro-2,2-dimethyl-trans-3-hydroxy-4-(2-phenoxy-3-carbonylethoxy-2-E-propen-1-yl)amino-2H-1-benzopyran; and 6-nitro-3,4-dihydro-2,2-dimethyl-trans-3-hydroxy-4-[(1-phenylethoxy)-3-carbonylethoxy-2-E-propen-1-yl]-amino-2H-1-benzopyran.

EXAMPLE 1

Preparation of 6-cyano-3,4-dihydro-2,2-dimethyl-trans-3-hydroxy-4-(4-methoxy-2-oxo-3-pyrrolin-1-yl)-2H-1-benzopyran and Related Compounds of Formula (I)

A. A solution of 6-cyano-3,4-dihydro-2,2-dimethyl-3,4-epoxy-2H-1-benzopyran (15 g) and 4-methoxy-3-pyrrolin-2-one (8.5 g) in dimethylsulfoxide (40 ml) was stirred and sodium hydride (80% dispersion in oil, 2.2 g) was added. The mixture was stirred at room temperature for 5 hours. Water (50 ml) was slowly added, and the resulting solution extracted with ethyl acetate (2×50 ml). After drying the organic layer with sodium sulfate the solvent was removed under reduced pressure and the residual oil chromatographed on silica gel (4% methanol in methylene chloride). The product obtained was dissolved in diethylether and precipitated with pentane to afford 4 g of 6-cyano-3,4-dihydro-2,2-dimethyl-trans-3-hydroxy-4-(4-methoxy-2-oxo-3-pyrrolin-1-yl)-2H-1-benzopyran, m.p. 256° C.

B. Similarly, replacing 4-methoxy-3-pyrrolin-2-one with the appropriate compound of formula (3), the following compounds of formula (I) were prepared:

6-cyano-3,4-dihydro-2,2-dimethyl-trans-3-hydroxy-4-(4-ethoxy-2-oxo-3-pyrrolin-1-yl)-2H-1-benzopyran, m.p. 225° C.;

6-cyano-3,4-dihydro-2,2-dimethyl-trans-3-hydroxy-4-(4-benzyloxy-2-oxo-3-pyrrolin-1-yl)-2H-1-benzopyran, m.p. 248° C.;

6-cyano-3,4-dihydro-2,2-dimethyl-trans-3-hydroxy-4-(4-iso-butoxy-2-oxo-3-pyrrolin-1-yl)-2H-1-benzopyran, m.p. 235° C.; and 6-cyano-3,4-dihydro-2,2-dimethyl-trans-3-hydroxy-4-(4-octyloxy-2-oxo-3-pyrrolin-1-yl)-2H-1-benzopyran, m.p. 158° C.

C. Similarly, optionally replacing 6-cyano-3,4-dihydro-2,2-dimethyl-3,4-epoxy-2H-1-benzopyran with the appropriate compound of formula (2), and optionally replacing 4-methoxy-3-pyrrolin-2-one with the appropriate compound of formula (3), the following compounds of formula (I) are prepared:

6-cyano-3,4-dihydro-2,2-dimethyl-trans-3-hydroxy-4-(4-n-propoxy-2-oxo-3-pyrrolin-1-yl)-2H-1-benzopyran;

6-cyano-3,4-dihydro-2,2-dimethyl-trans-3-hydroxy-4-(4-iso-propoxy-2-oxo-3-pyrrolin-1-yl)-2H-1-benzopyran;

6-cyano-3,4-dihydro-2,2-dimethyl-trans-3-hydroxy-4-(4-n-butoxy-2-oxo-3-pyrrolin-1-yl)-2H-1-benzopyran;

6-cyano-3,4-dihydro-2,2-dimethyl-trans-3-hydroxy-4-(4-t-butoxy-2-oxo-3-pyrrolin-1-yl)-2H-1-benzopyran;

6-cyano-3,4-dihydro-2,2-dimethyl-trans-3-hydroxy-4-(4-n-hexyloxy-2-oxo-3-pyrrolin-1-yl)-2H-1-benzopyran;

6-cyano-3,4-dihydro-2,2-dimethyl-trans-3-hydroxy-4-(4-dodecyloxy-2-oxo-3-pyrrolin-1-yl)-2H-1-benzopyran;

6-cyano-3,4-dihydro-2-methyl-trans-3-hydroxy-4-(4-ethoxy-2-oxo-3-pyrrolin-1-yl)-2H-1-benzopyran;

6-cyano-3,4-dihydro-2-ethyl-trans-3-hydroxy-4-(4-ethoxy-2-oxo-3-pyrrolin-1-yl)-2H-1-benzopyran;

6-cyano-3,4-dihydro-2-n-butyl-trans-3-hydroxy-4-(4-ethoxy-2-oxo-3-pyrrolin-1-yl)-2H-1-benzopyran;

6-cyano-3,4-dihydro-2-methyl-2-ethyl-trans-3-hydroxy-4-(4-ethoxy-2-oxo-3-pyrrolin-1-yl)-2H-1-benzopyran;

6-cyano-3,4-dihydro-2,2-diethyl-trans-3-hydroxy-4-(4-methoxy-2-oxo-3-pyrrolin-1-yl)-2H-1-benzopyran;
6-cyano-3,4-dihydro-2,2-diethyl-trans-3-hydroxy-4-(4-ethoxy-2-oxo-3-pyrrolin-1-yl)-2H-1-benzopyran;
6-cyano-3,4-dihydro-2,2-diethyl-trans-3-hydroxy-4-(4-n-hexyloxy-2-oxo-3-pyrrolin-1-yl)-2H-1-benzopyran;
6-cyano-3,4-dihydro-2,2-di-n-butyl-trans-3-hydroxy-4-(4-ethoxy-2-oxo-3-pyrrolin-1-yl)-2H-1-benzopyran;
6-cyano-3,4-dihydro-2,2-dimethyl-trans-3-hydroxy-4-(4-vinyloxy-2-oxo-3-pyrrolin-1-yl)-2H-1-benzopyran;
6-cyano-3,4-dihydro-2,2-dimethyl-trans-3-hydroxy-4-(4-allyloxy-2-oxo-3-pyrrolin-1-yl)-2H-1-benzopyran;
6-cyano-3,4-dihydro-2,2-dimethyl-trans-3-hydroxy-4-[4-(but-3-en-1-yl)oxy-2-oxo-3-pyrrolin-1-yl]-2H-1-benzopyran;
6-cyano-3,4-dihydro-2,2-dimethyl-trans-3-hydroxy-4-(4-phenoxy-2-oxo-3-pyrrolin-1-yl)-2H-1-benzopyran;
6-cyano-3,4-dihydro-2,2-dimethyl-trans-3-hydroxy-4-[4-(1-phenylethoxy)-2-oxo-3-pyrrolin-1-yl]-2H-1-benzopyran;
6-nitro-3,4-dihydro-2,2-dimethyl-trans-3-hydroxy-4-(4-benzyloxy-2-oxo-3-pyrrolin-1-yl)-2H-1-benzopyran;
6-nitro-3,4-dihydro-2,2-dimethyl-trans-3-hydroxy-4-(4-methoxy-2-oxo-3-pyrrolin-1-yl)-2H-1-benzopyran;
6-nitro-3,4-dihydro-2,2-dimethyl-trans-3-hydroxy-4-(4-ethoxy-2-oxo-3-pyrrolin-1-yl)-2H-1-benzopyran;
6-nitro-3,4-dihydro-2,2-dimethyl-trans-3-hydroxy-4-(4-n-propoxy-2-oxo-3-pyrrolin-1-yl)-2H-1-benzopyran;
6-nitro-3,4-dihydro-2,2-dimethyl-trans-3-hydroxy-4-(4-iso-propoxy-2-oxo-3-pyrrolin-1-yl)-2H-1-benzopyran;
6-nitro-3,4-dihydro-2,2-dimethyl-trans-3-hydroxy-4-(4-n-butoxy-2-oxo-3-pyrrolin-1-yl)-2H-1-benzopyran;
6-nitro-3,4-dihydro-2,2-dimethyl-trans-3-hydroxy-4-(4-t-butoxy-2-oxo-3-pyrrolin-1-yl)-2H-1-benzopyran;
6-nitro-3,4-dihydro-2,2-dimethyl-trans-3-hydroxy-4-(4-n-hexyloxy-2-oxo-3-pyrrolin-1-yl)-2H-1-benzopyran;
6-nitro-3,4-dihydro-2,2-dimethyl-trans-3-hydroxy-4-(4-dodecyloxy-2-oxo-3-pyrrolin-1-yl)-2H-1-benzopyran;
6-nitro-3,4-dihydro-2-methyl-trans-3-hydroxy-4-(4-ethoxy-2-oxo-3-pyrrolin-1-yl)-2H-1-benzopyran;
6-nitro-3,4-dihydro-2-ethyl-trans-3-hydroxy-4-(4-ethoxy-2-oxo-3-pyrrolin-1-yl)-2H-1-benzopyran;
6-nitro-3,4-dihydro-2-n-butyl-trans-3-hydroxy-4-(4-ethoxy-2-oxo-3-pyrrolin-1-yl)-2H-1-benzopyran;
6-nitro-3,4-dihydro-2-methyl-2-ethyl-trans-3-hydroxy-4-(4-ethoxy-2-oxo-3-pyrrolin-1-yl)-2H-1-benzopyran;
6-nitro-3,4-dihydro-2,2-diethyl-trans-3-hydroxy-4-(4-methoxy-2-oxo-3-pyrrolin-1-yl)-2H-1-benzopyran;
6-nitro-3,4-dihydro-2,2-diethyl-trans-3-hydroxy-4-(4-ethoxy-2-oxo-3-pyrrolin-1-yl)-2H-1-benzopyran;
6-nitro-3,4-dihydro-2,2-diethyl-trans-3-hydroxy-4-(4-n-hexyloxy-2-oxo-3-pyrrolin-1-yl)-2H-1-benzopyran;
6-nitro-3,4-dihydro-2,2-di-n-butyl-trans-3-hydroxy-4-(4-ethoxy-2-oxo-3-pyrrolin-1-yl)-2H-1-benzopyran;
6-nitro-3,4-dihydro-2,2-dimethyl-trans-3-hydroxy-4-(4-vinyloxy-2-oxo-3-pyrrolin-1-yl)-2H-1-benzopyran;
6-nitro-3,4-dihydro-2,2-dimethyl-trans-3-hydroxy-4-(4-allyloxy-2-oxo-3-pyrrolin-1-yl)-2H-1-benzopyran; and
6-nitro-3,4-dihydro-2,2-dimethyl-trans-3-hydroxy-4-[4-(but-3-en-1-yl)oxy-2-oxo-3-pyrrolin-1-yl]-2H-1-benzopyran.

EXAMPLE 2

Preparation of
6-cyano-3,4-dihydro-2,2-dimethyl-trans-3-hydroxy-4-(4-benzyloxy-2-oxo-3-pyrrolin-1-yl)-2H-1-benzopyran
and Related Compounds of Formula (I)

A. A mixture of 6-cyano-3,4-dihydro-2,2-dimethyl-trans-3-hydroxy-4-(4-methoxy-2-oxo-3-pyrrolin-1-yl)-2H-1-benzopyran (0.7 g), benzyl alcohol (0.92 ml) and methanesulfonic acid (0.01 g) was heated at 80° C. for 3 hours under reduced pressure (40 mbars). After cooling the residue was stirred with diethylether, and the insoluble product filtered off and washed twice with diethylether, to give 6-cyano-3,4-dihydro-2,2-dimethyl-trans-3-hydroxy-4-(4-benzyloxy-2-oxo-3-pyrrolin-1-yl)-2H-1-benzopyran, m.p. 248° C.

B. Alternatively, a mixture of 6-cyano-3,4-dihydro-2,2-dimethyl-trans-3-hydroxy-4-(4-methoxy-2-oxo-3-pyrrolin-1-yl)-2H-1-benzopyran (0.7 g), benzyl alcohol (0.92 ml) and methanesulfonic acid (0.01 g) was refluxed for 2 hours in the presence of 3A molecular sieves. After cooling the molecular sieves were filtered off, the filtrate stirred with diethylether, the insoluble product filtered off and washed twice with diethylether, to give 6-cyano-3,4-dihydro-2,2-dimethyl-trans-3-hydroxy-4-(4-benzyloxy-2-oxo-3-pyrrolin-1-yl)-2H-1-benzopyran, m.p. 248° C.

C. Similarly, replacing benzyl alcohol with the appropriate alcohol of formula $R_4OH$ and following the procedures of 2A or 2B above, the following compounds of formula (I) were prepared:
6-cyano-3,4-dihydro-2,2-dimethyl-trans-3-hydroxy-4-(4-n-propoxy-2-oxo-3-pyrrolin-1-yl)-2H-1-benzopyran, m.p. 210° C.;
6-cyano-3,4-dihydro-2,2-dimethyl-trans-3-hydroxy-4-(4-iso-propoxy-2-oxo-3-pyrrolin-1-yl)-2H-1-benzopyran, m.p. 246° C.;
6-cyano-3,4-dihydro-2,2-dimethyl-trans-3-hydroxy-4-(4-allyloxy-2-oxo-3-pyrrolin-1-yl)-2H-1-benzopyran, m.p. 208° C.;
6-cyano-3,4-dihydro-2,2-dimethyl-trans-3-hydroxy-4-(4-n-butoxy-2-oxo-3-pyrrolin-1-yl)-2H-1-benzopyran, m.p. 220° C.; and
6-cyano-3,4-dihydro-2,2-dimethyl-trans-3-hydroxy-4-[4-(3-N,N-diethylaminopropoxy)-2-oxo-3-pyrrolin-1-yl]-2H-1-benzopyran hydrochloride, m.p. 210° C.

D. Similarly, optionally replacing 6-cyano-3,4-dihydro-2,2-dimethyl-trans-3-hydroxy-4-(4-methoxy-2-oxo-3-pyrrolin-1-yl)-2H-1-benzopyran with the appropriate optically active or racemic compound of formula (I), and optionally replacing benzyl alcohol with the appropriate compound of formula $R_4OH$, the following compounds of formula (I) are prepared as the (−) or (+) optical isomer or as a racemic mixture:
6-cyano-3,4-dihydro-2,2-dimethyl-trans-3-hydroxy-4-(4-benzyloxy-2-oxo-3-pyrrolin-1-yl)-2H-1-benzopyran;
6-cyano-3,4-dihydro-2,2-dimethyl-trans-3-hydroxy-4-(4-n-propoxy-2-oxo-3-pyrrolin-1-yl)-2H-1-benzopyran;
6-cyano-3,4-dihydro-2,2-dimethyl-trans-3-hydroxy-4-(4-iso-propoxy-2-oxo-3-pyrrolin-1-yl)-2H-1-benzopyran;
6-cyano-3,4-dihydro-2,2-dimethyl-trans-3-hydroxy-4-(4-allyloxy-2-oxo-3-pyrrolin-1-yl)-2H-1-benzopyran;
6-cyano-3,4-dihydro-2,2-dimethyl-trans-3-hydroxy-4-(4-n-butoxy-2-oxo-3-pyrrolin-1-yl)-2H-1-benzopyran;

6-cyano-3,4-dihydro-2,2-dimethyl-trans-3-hydroxy-4-[4-(3-N,N-diethylaminopropoxy)-2-oxo-3-pyrrolin-1-yl]-2H-1-benzopyran;
6-cyano-3,4-dihydro-2,2-dimethyl-trans-3-hydroxy-4-(4-benzyloxy-2-oxo-3-pyrrolin-1-yl)-2H-1-benzopyran;
6-cyano-3,4-dihydro-2,2-dimethyl-trans-3-hydroxy-4-(4-iso-butoxy-2-oxo-3-pyrrolin-1-yl)-2H-1-benzopyran;
6-cyano-3,4-dihydro-2,2-dimethyl-trans-3-hydroxy-4-(4-octyloxy-2-oxo-3-pyrrolin-1-yl)-2H-1-benzopyran;
6-cyano-3,4-dihydro-2,2-dimethyl-trans-3-hydroxy-4-(4-n-propoxy-2-oxo-3-pyrrolin-1-yl)-2H-1-benzopyran;
6-cyano-3,4-dihydro-2,2-dimethyl-trans-3-hydroxy-4-(4-iso-propoxy-2-oxo-3-pyrrolin-1-yl)-2H-1-benzopyran;
6-cyano-3,4-dihydro-2,2-dimethyl-trans-3-hydroxy-4-(4-n-butoxy-2-oxo-3-pyrrolin-1-yl)-2H-1-benzopyran;
6-cyano-3,4-dihydro-2,2-dimethyl-trans-3-hydroxy-4-(4-t-butoxy-2-oxo-3-pyrrolin-1-yl)-2H-1-benzopyran;
6-cyano-3,4-dihydro-2,2-dimethyl-trans-3-hydroxy-4-(4-n-hexyloxy-2-oxo-3-pyrrolin-1-yl)-2H-1-benzopyran;
6-cyano-3,4-dihydro-2,2-dimethyl-trans-3-hydroxy-4-(4-dodecyloxy-2-oxo-3-pyrrolin-1-yl)-2H-1-benzopyran;
6-cyano-3,4-dihydro-2,2-diethyl-trans-3-hydroxy-4-(4-n-hexyloxy-2-oxo-3-pyrrolin-1-yl)-2H-1-benzopyran;
6-cyano-3,4-dihydro-2,2-dimethyl-trans-3-hydroxy-4-(4-vinyloxy-2-oxo-3-pyrrolin-1-yl)-2H-1-benzopyran;
6-cyano-3,4-dihydro-2,2-dimethyl-trans-3-hydroxy-4-[4-(but-3-en-1-yl)oxy-2-oxo-3-pyrrolin-1-yl]-2H-1-benzopyran;
6-cyano-3,4-dihydro-2,2-dimethyl-trans-3-hydroxy-4-(4-phenoxy-2-oxo-3-pyrrolin-1-yl)-2H-1-benzopyran;
6-cyano-3,4-dihydro-2,2-dimethyl-trans-3-hydroxy-4-[4-(1-phenylethoxy)-2-oxo-3-pyrrolin-1-yl]-2H-1-benzopyran;
6-cyano-3,4-dihydro-2,2-dimethyl-trans-3-hydroxy-4-[4-(3-methoxypropoxy)-2-oxo-3-pyrrolin-1-yl]-2H-1-benzopyran;
6-nitro-3,4-dihydro-2,2-dimethyl-trans-3-hydroxy-4-(4-benzyloxy-2-oxo-3-pyrrolin-1-yl)-2H-1-benzopyran;
6-nitro-3,4-dihydro-2,2-dimethyl-trans-3-hydroxy-4-(4-n-propoxy-2-oxo-3-pyrrolin-1-yl)-2H-1-benzopyran;
6-nitro-3,4-dihydro-2,2-dimethyl-trans-3-hydroxy-4-(4-iso-propoxy-2-oxo-3-pyrrolin-1-yl)-2H-1-benzopyran;
6-nitro-3,4-dihydro-2,2-dimethyl-trans-3-hydroxy-4-(4-n-butoxy-2-oxo-3-pyrrolin-1-yl)-2H-1-benzopyran;
6-nitro-3,4-dihydro-2,2-dimethyl-trans-3-hydroxy-4-(4-t-butoxy-2-oxo-3-pyrrolin-1-yl)-2H-1-benzopyran;
6-nitro-3,4-dihydro-2,2-dimethyl-trans-3-hydroxy-4-(4-n-hexyloxy-2-oxo-3-pyrrolin-1-yl)-2H-1-benzopyran;
6-nitro-3,4-dihydro-2,2-dimethyl-trans-3-hydroxy-4-(4-dodecyloxy-2-oxo-3-pyrrolin-1-yl)-2H-1-benzopyran;
6-nitro-3,4-dihydro-2,2-diethyl-trans-3-hydroxy-4-(4-n-hexyloxy-2-oxo-3-pyrrolin-1-yl)-2H-1-benzopyran;
6-nitro-3,4-dihydro-2,2-dimethyl-trans-3-hydroxy-4-(4-vinyloxy-2-oxo-3-pyrrolin-1-yl)-2H-1-benzopyran;
6-nitro-3,4-dihydro-2,2-dimethyl-trans-3-hydroxy-4-(4-allyloxy-2-oxo-3-pyrrolin-1-yl)-2H-1-benzopyran; and
6-nitro-3,4-dihydro-2,2-dimethyl-trans-3-hydroxy-4-[4-(but-3-en-1-yl)oxy-2-oxo-3-pyrrolin-1-yl]-2H-1-benzopyran.

EXAMPLE 3

Preparation of (−)-6-cyano-3,4-dihydro-2,2-dimethyl-trans-3-hydroxy-4-(4-ethoxy-2-oxo-3-pyrrolin-1-yl)-2H-1-benzopyran and Related Compounds of Formula (I)

A. A mixture of (+)-6-cyano-3,4-dihydro-2,2-dimethyl-trans-3-hydroxy-4-(2-ethoxy-3-carbonylethoxy-2-E-propen-1-yl)amino-2H-1-benzopyran (2.05 g) and 40 ml of xylene was refluxed for 15 hours. Xylene was removed under reduced pressure and the residue purified by flash chromatography on silica gel, eluting with 3% methanol/methylene chloride. The product was triturated in diethyl ether, to give 0.46 g of the pure (−)-6-cyano-3,4-dihydro-2,2-dimethyl-trans-3-hydroxy-4-(4-ethoxy-2-oxo-3-pyrrolin-1-yl)-2H-1-benzopyran, mp 210° C., $[\alpha]_D^{25} = -20.71$ (c=0.95, ethanol).

B. Similarly, replacing (+)-6-cyano-3,4-dihydro-2,2-dimethyl-trans-3-hydroxy-4-(2-ethoxy-3-carbonylethoxy-2-E-propen-1-yl)amino-2H-1-benzopyran with the (−)-isomer, the following compound of formula (I) was prepared:

(+)-6-cyano-3,4-dihydro-2,2-dimethyl-trans-3-hydroxy-4-(4-ethoxy-2-oxo-3-pyrrolin-1-yl)-2H-1-benzopyran, mp 210° C., $[\alpha]_D^{25} = +20.29$ (c=0.97, ethanol).

C. Similarly, replacing (+)-6-cyano-3,4-dihydro-2,2-dimethyl-trans-3-hydroxy-4-(2-ethoxy-3-carbonylethoxy-2-E-propen-1-yl)amino-2H-1-benzopyran with the appropriate racemic compound of formula (6) the following racemic compounds of formula (I) were prepared:

6-cyano-3,4-dihydro-2,2-dimethyl-trans-3-hydroxy-4-(4-methoxy-2-oxo-3-pyrrolin-1-yl)-2H-1-benzopyran, m.p. 256° C.; and 6-cyano-3,4-dihydro-2,2-dimethyl-trans-3-hydroxy-4-(4-ethoxy-2-oxo-3-pyrrolin-1-yl)-2H-1-benzopyran, m.p. 225° C.

D. Similarly, replacing (+)-6-cyano-3,4-dihydro-2,2-dimethyl-trans-3-hydroxy-4-(2-ethoxy-3-carbonylethoxy-2-E-propen-1-yl)amino-2H-1-benzopyran with the appropriate optically active or racemic compound of formula (6) the following compounds of formula (I) are prepared as the (−) or (+) optical isomer or as a racemic mixture:

6-cyano-3,4-dihydro-2,2-dimethyl-trans-3-hydroxy-4-(4-methoxy-2-oxo-3-pyrrolin-1-yl)-2H-1-benzopyran;
6-cyano-3,4-dihydro-2,2-dimethyl-trans-3-hydroxy-4-(4-benzyloxy-2-oxo-3-pyrrolin-1-yl)-2H-1-benzopyran;
6-cyano-3,4-dihydro-2,2-dimethyl-trans-3-hydroxy-4-(4-iso-butoxy-2-oxo-3-pyrrolin-1-yl)-2H-1-benzopyran;
6-cyano-3,4-dihydro-2,2-dimethyl-trans-3-hydroxy-4-(4-octyloxy-2-oxo-3-pyrrolin-1-yl)-2H-1-benzopyran;
6-cyano-3,4-dihydro-2,2-dimethyl-trans-3-hydroxy-4-(4-n-propoxy-2-oxo-3-pyrrolin-1-yl)-2H-1-benzopyran;
6-cyano-3,4-dihydro-2,2-dimethyl-trans-3-hydroxy-4-(4-iso-propoxy-2-oxo-3-pyrrolin-1-yl)-2H-1-benzopyran;
6-cyano-3,4-dihydro-2,2-dimethyl-trans-3-hydroxy-4-(4-n-butoxy-2-oxo-3-pyrrolin-1-yl)-2H-1-benzopyran;
6-cyano-3,4-dihydro-2,2-dimethyl-trans-3-hydroxy-4-(4-t-butoxy-2-oxo-3-pyrrolin-1-yl)-2H-1-benzopyran;

6-cyano-3,4-dihydro-2,2-dimethyl-trans-3-hydroxy-4-(4-n-hexyloxy-2-oxo-3-pyrrolin-1-yl)-2H-1-benzopyran;

6-cyano-3,4-dihydro-2,2-dimethyl-trans-3-hydroxy-4-(4-dodecyloxy-2-oxo-3-pyrrolin-1-yl)-2H-1-benzopyran;

6-cyano-3,4-dihydro-2-methyl-trans-3-hydroxy-4-(4-ethoxy-2-oxo-3-pyrrolin-1-yl)-2H-1-benzopyran;

6-cyano-3,4-dihydro-2-ethyl-trans-3-hydroxy-4-(4-ethoxy-2-oxo-3-pyrrolin-1-yl)-2H-1-benzopyran;

6-cyano-3,4-dihydro-2-n-butyl-trans-3-hydroxy-4-(4-ethoxy-2-oxo-3-pyrrolin-1-yl)-2H-1-benzopyran;

6-cyano-3,4-dihydro-2-methyl-2-ethyl-trans-3-hydroxy-4-(4-ethoxy-2-oxo-3-pyrrolin-1-yl)-2H-1-benzopyran;

6-cyano-3,4-dihydro-2,2-diethyl-trans-3-hydroxy-4-(4-methoxy-2-oxo-3-pyrrolin-1-yl)-2H-1-benzopyran;

6-cyano-3,4-dihydro-2,2-diethyl-trans-3-hydroxy-4-(4-ethoxy-2-oxo-3-pyrrolin-1-yl)-2H-1-benzopyran;

6-cyano-3,4-dihydro-2,2-diethyl-trans-3-hydroxy-4-(4-n-hexyloxy-2-oxo-3-pyrrolin-1-yl)-2H-1-benzopyran;

6-cyano-3,4-dihydro-2,2-di-n-butyl-trans-3-hydroxy-4-(4-ethoxy-2-oxo-3-pyrrolin-1-yl)-2H-1-benzopyran;

6-cyano-3,4-dihydro-2,2-dimethyl-trans-3-hydroxy-4-(4-allyloxy-2-oxo-3-pyrrolin-1-yl)-2H-1-benzopyran;

6-cyano-3,4-dihydro-2,2-dimethyl-trans-3-hydroxy-4-[4-(but-3-en-1-yl)oxy-2-oxo-3-pyrrolin-1-yl]-2H-1-benzopyran;

6-cyano-3,4-dihydro-2,2-dimethyl-trans-3-hydroxy-4-(4-phenoxy-2-oxo-3-pyrrolin-1-yl)-2H-1-benzopyran;

6-cyano-3,4-dihydro-2,2-dimethyl-trans-3-hydroxy-4-[4-(1-phenylethoxy)-2-oxo-3-pyrrolin-1-yl]-2H-1-benzopyran;

6-nitro-3,4-dihydro-2,2-dimethyl-trans-3-hydroxy-4-(4-benzyloxy-2-oxo-3-pyrrolin-1-yl)-2H-1-benzopyran;

6-nitro-3,4-dihydro-2,2-dimethyl-trans-3-hydroxy-4-(4-methoxy-2-oxo-3-pyrrolin-1-yl)-2H-1-benzopyran;

6-nitro-3,4-dihydro-2,2-dimethyl-trans-3-hydroxy-4-(4-ethoxy-2-oxo-3-pyrrolin-1-yl)-2H-1-benzopyran;

6-nitro-3,4-dihydro-2,2-dimethyl-trans-3-hydroxy-4-(4-n-propoxy-2-oxo-3-pyrrolin-1-yl)-2H-1-benzopyran;

6-nitro-3,4-dihydro-2,2-dimethyl-trans-3-hydroxy-4-(4-iso-propoxy-2-oxo-3-pyrrolin-1-yl)-2H-1-benzopyran;

6-nitro-3,4-dihydro-2,2-dimethyl-trans-3-hydroxy-4-(4-n-butoxy-2-oxo-3-pyrrolin-1-yl)-2H-1-benzopyran;

6-nitro-3,4-dihydro-2,2-dimethyl-trans-3-hydroxy-4-(4-t-butoxy-2-oxo-3-pyrrolin-1-yl)-2H-1-benzopyran;

6-nitro-3,4-dihydro-2,2-dimethyl-trans-3-hydroxy-4-(4-n-hexyloxy-2-oxo-3-pyrrolin-1-yl)-2H-1-benzopyran;

6-nitro-3,4-dihydro-2,2-dimethyl-trans-3-hydroxy-4-(4-dodecyloxy-2-oxo-3-pyrrolin-1-yl)-2H-1-benzopyran;

6-nitro-3,4-dihydro-2-methyl-trans-3-hydroxy-4-(4-ethoxy-2-oxo-3-pyrrolin-1-yl)-2H-1-benzopyran;

6-nitro-3,4-dihydro-2-ethyl-trans-3-hydroxy-4-(4-ethoxy-2-oxo-3-pyrrolin-1-yl)-2H-1-benzopyran;

6-nitro-3,4-dihydro-2-n-butyl-trans-3-hydroxy-4-(4-ethoxy-2-oxo-3-pyrrolin-1-yl)-2H-1-benzopyran;

6-nitro-3,4-dihydro-2-methyl-2-ethyl-trans-3-hydroxy-4-(4-ethoxy-2-oxo-3-pyrrolin-1-yl)-2H-1-benzopyran;

6-nitro-3,4-dihydro-2,2-diethyl-trans-3-hydroxy-4-(4-methoxy-2-oxo-3-pyrrolin-1-yl)-2H-1-benzopyran;

6-nitro-3,4-dihydro-2,2-diethyl-trans-3-hydroxy-4-(4-ethoxy-2-oxo-3-pyrrolin-1-yl)-2H-1-benzopyran;

6-nitro-3,4-dihydro-2,2-diethyl-trans-3-hydroxy-4-(4-n-hexyloxy-2-oxo-3-pyrrolin-1-yl)-2H-1-benzopyran;

6-nitro-3,4-dihydro-2,2-di-n-butyl-trans-3-hydroxy-4-(4-ethoxy-2-oxo-3-pyrrolin-1-yl)-2H-1-benzopyran;

6-nitro-3,4-dihydro-2,2-dimethyl-trans-3-hydroxy-4-(4-allyloxy-2-oxo-3-pyrrolin-1-yl)-2H-1-benzopyran; and 6-nitro-3,4-dihydro-2,2-dimethyl-trans-3-hydroxy-4-[4-(but-3-en-1-yl)oxy-2-oxo-3-pyrrolin-1-yl]-2H-1-benzopyran.

EXAMPLE 4

Preparation of 6-cyano-3,4-dihydro-2,2-dimethyl-trans-3-acetyloxy-4-(4-ethoxy-2-oxo-3-pyrrolin-1-yl)-2H-1-benzopyran and Related Pharmaceutically Acceptable Esters of the Compounds of Formula (I)

A. To a suspension of 6-cyano-3,4-dihydro-2,2-dimethyl-trans-3-hydroxy-4-(4-ethoxy-2-oxo-3-pyrrolin-1-yl)-2H-1-benzopyran (0.5 g) in 25 ml of methylene chloride at 0° C. was added pyridine (0.415 g) and acetic anhydride (0.56 g), and the mixture stirred at room temperature for 5 days. The reaction mixture was then stirred with a mixture of 50 ml of water and 40 ml of methylene chloride. The organic layer was separated, washed with water, dried over anhydrous sodium sulfate and solvent removed under reduced pressure. The residue was triturated with ether followed by pentane to give 6-cyano-3,4-dihydro-2,2-dimethyl-trans-3-acetyloxy-4-(4-ethoxy-2-oxo-3-pyrrolin-1-yl)-2H-1-benzopyran, m.p. 156° C.

B. Similarly, replacing 6-cyano-3,4-dihydro-2,2-dimethyl-trans-3-hydroxy-4-(4-ethoxy-2-oxo-3-pyrrolin-1-yl)-2H-1-benzopyran with the appropriate compound of formula (I), the following compounds of formula (I) are prepared:

6-cyano-3,4-dihydro-2,2-dimethyl-trans-3-acetyloxy-4-(4-methoxy-2-oxo-3-pyrrolin-1-yl)-2H-1-benzopyran;

6-cyano-3,4-dihydro-2,2-dimethyl-trans-3-acetyloxy-4-(4-benzyloxy-2-oxo-3-pyrrolin-1-yl)-2H-1-benzopyran;

6-cyano-3,4-dihydro-2,2-dimethyl-trans-3-acetyloxy-4-(4-iso-butoxy-2-oxo-3-pyrrolin-1-yl)-2H-1-benzopyran;

6-cyano-3,4-dihydro-2,2-dimethyl-trans-3-acetyloxy-4-(4-octyloxy-2-oxo-3-pyrrolin-1-yl)-2H-1-benzopyran;

6-cyano-3,4-dihydro-2,2-dimethyl-trans-3-acetyloxy-4-(4-n-propoxy-2-oxo-3-pyrrolin-1-yl)-2H-1-benzopyran;

6-cyano-3,4-dihydro-2,2-dimethyl-trans-3-acetyloxy-4-(4-iso-propoxy-2-oxo-3-pyrrolin-1-yl)-2H-1-benzopyran;

6-cyano-3,4-dihydro-2,2-dimethyl-trans-3-acetyloxy-4-(4-n-butoxy-2-oxo-3-pyrrolin-1-yl)-2H-1-benzopyran;

6-cyano-3,4-dihydro-2,2-dimethyl-trans-3-acetyloxy-4-(4-t-butoxy-2-oxo-3-pyrrolin-1-yl)-2H-1-benzopyran;

6-cyano-3,4-dihydro-2,2-dimethyl-trans-3-acetyloxy-4-(4-n-hexyloxy-2-oxo-3-pyrrolin-1-yl)-2H-1-benzopyran;

6-cyano-3,4-dihydro-2,2-dimethyl-trans-3-acetyloxy-4-(4-dodecyloxy-2-oxo-3-pyrrolin-1-yl)-2H-1-benzopyran;

6-cyano-3,4-dihydro-2-methyl-trans-3-acetyloxy-4-(4-ethoxy-2-oxo-3-pyrrolin-1-yl)-2H-1-benzopyran;

6-cyano-3,4-dihydro-2-ethyl-trans-3-acetyloxy-4-(4-ethoxy-2-oxo-3-pyrrolin-1-yl)-2H-1-benzopyran;

6-cyano-3,4-dihydro-2-n-butyl-trans-3-acetyloxy-4-(4-ethoxy-2-oxo-3-pyrrolin-1-yl)-2H-1-benzopyran;

6-cyano-3,4-dihydro-2-methyl-2-ethyl-trans-3-acetyloxy-4-(4-ethoxy-2-oxo-3-pyrrolin-1-yl)-2H-1-benzopyran;

6-cyano-3,4-dihydro-2,2-diethyl-trans-3-acetyloxy-4-(4-methoxy-2-oxo-3-pyrrolin-1-yl)-2H-1-benzopyran;
6-cyano-3,4-dihydro-2,2-diethyl-trans-3-acetyloxy-4-(4-ethoxy-2-oxo-3-pyrrolin-1-yl)-2H-1-benzopyran;
6-cyano-3,4-dihydro-2,2-diethyl-trans-3-acetyloxy-4-(4-n-hexyloxy-2-oxo-3-pyrrolin-1-yl)-2H-1-benzopyran;
6-cyano-3,4-dihydro-2,2-di-n-butyl-trans-3-acetyloxy-4-(4-ethoxy-2-oxo-3-pyrrolin-1-yl)-2H-1-benzopyran;
6-cyano-3,4-dihydro-2,2-dimethyl-trans-3-acetyloxy-4-(4-allyloxy-2-oxo-3-pyrrolin-1-yl)-2H-1-benzopyran;
6-cyano-3,4-dihydro-2,2-dimethyl-trans-3-acetyloxy-4-[4-(but-3-en-1-yl)oxy-2-oxo-3-pyrrolin-1-yl]-2H-1-benzopyran;
6-cyano-3,4-dihydro-2,2-dimethyl-trans-3-acetyloxy-4-(4-phenoxy-2-oxo-3-pyrrolin-1-yl)-2H-1-benzopyran;
6-cyano-3,4-dihydro-2,2-dimethyl-trans-3-acetyloxy-4-[4-(1-phenylethoxy)-2-oxo-3-pyrrolin-1-yl]-2H-1-benzopyran;
6-nitro-3,4-dihydro-2,2-dimethyl-trans-3-acetyloxy-4-(4-benzyloxy-2-oxo-3-pyrrolin-1-yl)-2H-1-benzopyran;
6-nitro-3,4-dihydro-2,2-dimethyl-trans-3-acetyloxy-4-(4-methoxy-2-oxo-3-pyrrolin-1-yl)-2H-1-benzopyran;
6-nitro-3,4-dihydro-2,2-dimethyl-trans-3-acetyloxy-4-(4-ethoxy-2-oxo-3-pyrrolin-1-yl)-2H-1-benzopyran;
6-nitro-3,4-dihydro-2,2-dimethyl-trans-3-acetyloxy-4-(4-n-propoxy-2-oxo-3-pyrrolin-1-yl)-2H-1-benzopyran;
6-nitro-3,4-dihydro-2,2-dimethyl-trans-3-acetyloxy-4-(4-iso-propoxy-2-oxo-3-pyrrolin-1-yl)-2H-1-benzopyran;
6-nitro-3,4-dihydro-2,2-dimethyl-trans-3-acetyloxy-4-(4-n-butoxy-2-oxo-3-pyrrolin-1-yl)-2H-1-benzopyran;
6-nitro-3,4-dihydro-2,2-dimethyl-trans-3-acetyloxy-4-(4-t-butoxy-2-oxo-3-pyrrolin-1-yl)-2H-1-benzopyran;
6-nitro-3,4-dihydro-2,2-dimethyl-trans-3-acetyloxy-4-(4-n-hexyloxy-2-oxo-3-pyrrolin-1-yl)-2H-1-benzopyran;
6-nitro-3,4-dihydro-2,2-dimethyl-trans-3-acetyloxy-4-(4-dodecyloxy-2-oxo-3-pyrrolin-1-yl)-2H-1-benzopyran;
6-nitro-3,4-dihydro-2-methyl-trans-3-acetyloxy-4-(4-ethoxy-2-oxo-3-pyrrolin-1-yl)-2H-1-benzopyran;
6-nitro-3,4-dihydro-2-ethyl-trans-3-acetyloxy-4-(4-ethoxy-2-oxo-3-pyrrolin-1-yl)-2H-1-benzopyran;
6-nitro-3,4-dihydro-2-n-butyl-trans-3-acetyloxy-4-(4-ethoxy-2-oxo-3-pyrrolin-1-yl)-2H-1-benzopyran;
6-nitro-3,4-dihydro-2-methyl-2-ethyl-trans-3-acetyloxy-4-(4-ethoxy-2-oxo-3-pyrrolin-1-yl)-2H-1-benzopyran;
6-nitro-3,4-dihydro-2,2-diethyl-trans-3-acetyloxy-4-(4-methoxy-2-oxo-3-pyrrolin-1-yl)-2H-1-benzopyran;
6-nitro-3,4-dihydro-2,2-diethyl-trans-3-acetyloxy-4-(4-ethoxy-2-oxo-3-pyrrolin-1-yl)-2H-1-benzopyran;
6-nitro-3,4-dihydro-2,2-diethyl-trans-3-acetyloxy-4-(4-n-hexyloxy-2-oxo-3-pyrrolin-1-yl)-2H-1-benzopyran;
6-nitro-3,4-dihydro-2,2-di-n-butyl-trans-3-acetyloxy-4-(4-ethoxy-2-oxo-3-pyrrolin-1-yl)-2H-1-benzopyran;
6-nitro-3,4-dihydro-2,2-dimethyl-trans-3-acetyloxy-4-(4-allyloxy-2-oxo-3-pyrrolin-1-yl)-2H-1-benzopyran; and
6-nitro-3,4-dihydro-2,2-dimethyl-trans-3-acetyloxy-4-[4-(but-3-en-1-yl)oxy-2-oxo-3-pyrrolin-1-yl]-2H-1-benzopyran.

In Examples 5 through 9 the active ingredient is 6-cyano-3,4-dihydro-2,2-dimethyl-trans-3-hydroxy-4-(4-ethoxy-2-oxo-3-pyrrolin-1-yl)-2H-1-benzopyran. Other compounds of formula (I) may be substituted therein.

EXAMPLE 5

Composition for Oral Administration

| The composition contains: | % wt./wt. |
|---|---|
| Active ingredient | 20% |
| Lactose | 80% |

The two ingredients are milled, mixed and dispensed into capsules containing 100 mg each; one capsule would approximate a total daily dosage.

EXAMPLE 6

Composition for Oral Administration

| The composition contains: | % wt./wt. |
|---|---|
| Active ingredient | 20.0% |
| Magnesium stearate | 0.9% |
| Starch | 8.6% |
| Lactose | 79.6% |
| PVP (polyvinylpyrrolidine) | 0.9% |

The above ingredients with the exception of the magnesium stearate are combined and granulated using water as a granulating liquid. The formulation is then dried, mixed with the magnesium stearate and formed into tablets (containing 20 mg of active compound) with an appropriate tableting machine.

EXAMPLE 7

Parenteral Formulation (IV)

| The composition contains: | % wt./wt. |
|---|---|
| Active ingredient | 0.02 g |
| Propylene glycol | 20. g |
| Polyethylene glycol 400 | 20. g |
| Polysorbate 80 | 1. g |
| 0.9% Saline solution qs ad | 100 ml |

The active ingredient is dissolved in propylene glycol, polyethylene glycol 400 and polysorbate 80. A sufficient quantity of 0.9% saline solution is then added with stirring to provide 100 ml. of the I.V. solution which is filtered through a 0.2 micron membrane filter and packaged under sterile conditions.

EXAMPLE 8

Oral Solution Formulation

| The composition contains: | % wt./wt. |
|---|---|
| Active ingredient | 0.1 g |
| Propylene glycol | 20. g |
| Polyethylene glycol 400 | 20. g |
| Polysorbate 80 | 1. g |
| water to q.s. | 100 ml |

The active ingredient is dissolved in propylene glycol, polyethylene glycol 400 and polysorbate 80. A sufficient quantity of water is then added with stirring to provide 100 ml. of the solution which is filtered and bottled.

EXAMPLE 9

Suppository Formulation

| The composition contains: | % wt./wt. |
|---|---|
| Active ingredient | 1.0% |
| Polyethylene glycol 1000 | 74.5% |
| Polyethylene glycol 4000 | 24.5% |

The ingredients are melted together and mixed on a steam bath, and poured into molds containing 2.5 g total weight.

EXAMPLE 10

Determination of Smooth Muscle Relaxant Properties

The smooth muscle relaxant property of the compounds was evaluated in-vitro, using vascular preparations previously contracted with an appropriate spasmogen.

Aortas were quickly removed from either rats or rabbits killed by a blow to the head. The tissue was cleared of connective tissue and cut into helical strips after removing endothelium by gently rubbing with forceps. These strips were then bathed in Krebs physiological solution at 37° C., and saturated with a mixture of 95% oxygen/5% carbon dioxide under 1 g tension. Sustained contractions were evoked by adding barium chloride (1 mM). Contractile tension of the muscle strips was recorded isometrically. Test compounds were added at cumulatively increasing concentrations ($10^{-8}$ to $10^{-4}$M) in water or water with 2-3 drops Tween or 1% alcohol. The maximum reduction in barium induced-tension was compared for each differing concentration of test compounds used. The compounds of formula (I) demonstrated activity in this assay.

EXAMPLE 11

Determination of Antihypertensive Activity

The antihypertensive effects of the compounds of formula (I) were evaluated in spontaneously hypertensive rats (Charles River, aged 18 weeks)). The rats were anesthetized with pentobarbital (50 mg/Kg i.p.), and a catheter was implanted into the descending aorta via a carotid artery. The catheter was exteriorized at the back of the neck and sealed with a pin. After surgery the rats were housed in individual cages, and pulsatile aortic blood pressure was measured directly 2-5 days later in groups of 4-6 conscious animals, using a Statham P50 pressure tranducer connected to a Gould S8000 chart recorder. Heart rate was determined by using the pulse pressure to trigger a ratemeter. Rats with mean blood pressure greater than 150 mm Hg were considered to be hypertensive.

The test compounds were suspended in 2% Tween 80 vehicle for oral administration. A control group received vehicle (0.5 ml/Kg p.o.) alone. Cardiovascular parameters were recorded at 15, 30 and 45 minutes, and thereafter at hourly intervals for the first 7 hours, then at 24 hours post dosing. Maximum changes in systolic, diastolic and mean blood pressure were measured, as was change in heart rate. Calculations were made of the percentage changes in blood pressure and heart rate with respect to the initial values and vehicle-treated time controls. The duration of the antihypertensive effect was calculated as the time during which the blood pressure value remains significantly lower than the vehicle-treated group. The compounds of formula (I) demonstrated positive antihypertensive activity in this assay.

What is claimed is:

1. A compound represented by the formula:

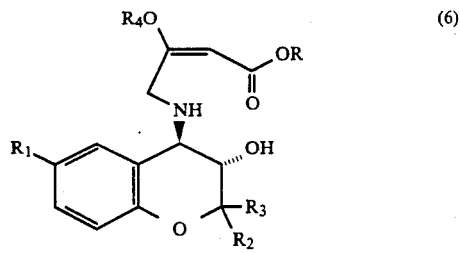

(6)

wherein:
  R is lower alkyl;
  $R_1$ is cyano or nitro;
  $R_2$ and $R_3$ are independently hydrogen or lower alkyl; and
  $R_4$ is alkyl; alkenyl; phenyl or phenyl-lower-alkyl in which any phenyl group may be optionally substituted with one or two substituents chosen from lower alkyl, lower alkoxy, halo, trifluoromethyl and hydroxy; —$(CH_2)_mOR_2$ or —$(CH_2)_mN(R_2)_2$; wherein m is an integer of 1-5 and $R_2$ is as defined above.

2. The compound of claim 1, wherein $R_1$ is cyano.

3. The compound of claim 2, wherein $R_2$ and $R_3$ are both methyl.

4. The compound of claim 3, wherein $R_4$ is lower alkyl.

5. The compound of claim 4, wherein $R_4$ is methyl.

6. The compound of claim 4, wherein $R_4$ is ethyl.

7. The compound of claim 3, wherein $R_4$ is lower alkenyl of 1-6 carbon atoms.

8. The compound of claim 3, wherein $R_4$ is phenyl-lower-alkyl.

* * * * *